United States Patent
Falk et al.

(10) Patent No.: US 9,884,349 B2
(45) Date of Patent: Feb. 6, 2018

(54) HOLDER PRODUCT RANGE AND CLEANING APPARATUS FOR CLEANING BREATHING APPARATUSES

(71) Applicant: MEIKO Maschinenbau GmbH & Co. KG, Offenburg (DE)

(72) Inventors: Herbert Falk, Offenburg (DE); Heiko Wörner, Bühl (DE)

(73) Assignee: MEIKO MASCHINENBAU GMBH & CO. KG, Offenburg (DE)

( * ) Notice: Subject to any disclaimer, the term of this patent is extended or adjusted under 35 U.S.C. 154(b) by 181 days.

(21) Appl. No.: 14/442,063

(22) PCT Filed: Nov. 11, 2013

(86) PCT No.: PCT/EP2013/073474
§ 371 (c)(1),
(2) Date: May 11, 2015

(87) PCT Pub. No.: WO2014/076026
PCT Pub. Date: May 22, 2014

(65) Prior Publication Data
US 2015/0314340 A1    Nov. 5, 2015

(30) Foreign Application Priority Data
Nov. 13, 2012   (DE) .................. 10 2012 220 646

(51) Int. Cl.
*B08B 3/02*  (2006.01)
*B08B 5/02*  (2006.01)
(Continued)

(52) U.S. Cl.
CPC ............ *B08B 5/02* (2013.01); *B08B 3/02* (2013.01); *B08B 3/04* (2013.01); *B08B 5/00* (2013.01);
(Continued)

(58) Field of Classification Search
CPC ...... A61M 16/06; A61M 2209/10; A61L 2/18; A61L 2202/17; A61L 2202/24;
(Continued)

(56) References Cited

U.S. PATENT DOCUMENTS

| 452,728 A | * | 5/1891 | Taylor | ............ G09F 3/00 346/146 |
| 3,881,503 A | | 5/1975 | Fox et al. | |

(Continued)

FOREIGN PATENT DOCUMENTS

| DE | 11 74 169 | 7/1964 |
| DE | 2 131 055 | 1/1972 |

(Continued)

OTHER PUBLICATIONS

International Preliminary Report on Patentability issued in related International Patent Application No. PCT/EP2013/073474, dated May 28, 2015.

(Continued)

*Primary Examiner* — Alexander Markoff
(74) *Attorney, Agent, or Firm* — Foley & Lardner LLP

(57) ABSTRACT

Proposed is a product range for cleaning breathing apparatuses, including at least two holders, wherein the holders include:
a first holder for cleaning breathing masks and breathing valves, including at least one mask holding device for positioning at least one breathing mask, additionally comprising at least one breathing valve holding device for positioning at least one breathing valve and least one pressurizing device with at least one pressure connection, wherein the pressure connection is connectable to the breathing valve and wherein the pressurizing device is set up to apply compressed air to the breathing valve during cleaning; and (Continued)

at least one second holder for cleaning carrying frameworks for pressurized gas cylinders for breather apparatuses, including at least one carrying framework holding device for positioning at least one carrying framework.

The holders are dimensioned in such a manner that they can be moved into a cleaning apparatus for cleaning the breathing apparatuses so as to be exchangeable.

17 Claims, 13 Drawing Sheets

(51) Int. Cl.
  *B08B 13/00* (2006.01)
  *B08B 3/04* (2006.01)
  *B08B 5/00* (2006.01)
  *A61M 16/06* (2006.01)
  *A61L 2/18* (2006.01)

(52) U.S. Cl.
  CPC .............. *B08B 13/00* (2013.01); *A61L 2/18* (2013.01); *A61L 2202/17* (2013.01); *A61L 2202/24* (2013.01); *A61M 16/06* (2013.01); *A61M 2209/10* (2013.01)

(58) Field of Classification Search
  CPC .... B08B 3/02; B08B 3/04; B08B 5/02; B08B 13/00; B08B 5/00
  See application file for complete search history.

(56) References Cited

U.S. PATENT DOCUMENTS

| | | | |
|---|---|---|---|
| 3,884,265 | A | 5/1975 | Fry et al. |
| 4,354,514 | A | 10/1982 | Sundheimer |
| 4,552,728 | A | 11/1985 | Taylor |
| 5,664,594 | A | 9/1997 | Kee |
| 6,334,341 | B1 | 1/2002 | Hellhake et al. |
| 6,571,811 | B2 | 6/2003 | Kabboush |
| 7,124,766 | B1 | 10/2006 | Hedgpeth |
| 9,308,558 | B2 * | 4/2016 | Ackermann ............ A62B 25/00 |
| 9,452,099 | B2 * | 9/2016 | Schneider ........... A47L 15/0015 |
| 9,527,117 | B2 * | 12/2016 | Ackermann ............ A62B 25/00 |
| 2005/0274624 | A1 | 12/2005 | Arata |
| 2009/0050181 | A1 | 2/2009 | Johansson |
| 2009/0183753 | A1 | 7/2009 | Maennie et al. |
| 2010/0175726 | A1 | 7/2010 | Eli |
| 2013/0074882 | A1 | 3/2013 | Ackermann et al. |

FOREIGN PATENT DOCUMENTS

| | | | |
|---|---|---|---|
| DE | 298 22 172 | 2/1999 | |
| DE | 200 03 744 | 7/2000 | |
| DE | 200 03 743 | 11/2000 | |
| DE | 100 20 835 A1 | 11/2001 | |
| DE | 10 2005 033 618 B3 | 11/2006 | |
| DE | 102005033618 B3 * | 11/2006 | ............... A61L 2/22 |
| DE | 10 2007 009 936 A1 | 9/2008 | |
| DE | 102007009936 A1 * | 9/2008 | ............... A61L 2/18 |
| DE | 10 2007 012 768 B4 | 1/2009 | |
| DE | 10 2010 029221 A1 | 2/2014 | |
| EP | 0 935 687 B1 | 8/1999 | |
| EP | 1 088 928 A1 | 4/2001 | |
| WO | WO 2011/144518 A2 | 11/2011 | |

OTHER PUBLICATIONS

International Search Report issued in related International Patent Application No. PCT/EP2013/073474, dated Feb. 20, 2014.
International Search Report and Written Opinion issued in PCT/EP2011/057706, dated Sep. 10, 2012 (English Translation also provided).
International Preliminary Report on Patentability issued in PCT/EP2011/057706, dated Dec. 13, 2012 (English Translation).
International Preliminary Report on Patentability issued in PCT/EP2011/057706, dated Dec. 6, 2012.

* cited by examiner

HOLDER PRODUCT RANGE AND CLEANING APPARATUS FOR CLEANING BREATHING APPARATUSES

SCOPE OF THE INVENTION

The invention relates to a product range of holders for breathing apparatuses as well as to a cleaning apparatus and to a method for cleaning breathing apparatuses. These types of product ranges, cleaning devices and methods are generally used for cleaning and as an option also additionally for sterilizing and/or disinfecting breathing apparatuses or also components parts of the same. In general, the devices and methods described within the framework of the present invention can be used, for example, to clean breathing apparatuses for rescue teams such as the fire service, technical relief organizations or paramedics. As an alternative to this or in addition to it, breathing apparatuses for divers or in general persons in hostile or critical working environments can also be cleaned. Consequently, the devices and methods according to the present invention can also be used, for example, within the framework of use by armed forces and security forces such as, for example, police officers. The proposed devices and methods can also be used in principle for breathing apparatuses in the medical sector, for example breathing masks for oxygen supply and operations. In particular, the cleaning of breathing masks or breathing valves in general is considered in the scope of application.

PRIOR ART

Breathing apparatuses such as, for example, breathing masks, in particular protective breathing masks, or breathing valves, are as a rule a component part of the personal protective equipment of, for example, rescue workers, armed forces or security forces. Thus, a plurality of breathing apparatuses for different applications are known from the prior art. For example, rescue teams such as the fire services use protective breathing masks with filters for removing harmful constituents from the breathing air drawn in. In many cases, however, as an alternative to a filter or in addition to it, a so-called breathing valve is used, by means of which the user can be respirated with a breathing gas, for example compressed air. Breathing valves, which are frequently also designated as breathing regulators, make it possible in general for a user to breathe from a pressurized gas cylinder or another pressurized gas connection and in this way to stay, for example, under water or in another non-breathable or toxic atmosphere. To this end, the pressurized gas, for example compressed air, out of the pressurized gas connection through the breathing valve is adapted to a pressure prevailing in an operating environment of the user.

The breathing apparatuses or component parts thereof, as a rule, have to be cleaned, sterilized, dried, tested and where applicable repaired and packed after each use. By way of the cleaning all contamination as a result of use or storage is to be removed such that the breathing apparatuses can be provided macroscopically clean and impeccably hygienic, for example for the next steps of a preparation. These same requirements are also applicable as a rule to other component parts of breathing apparatuses, such as, for example, set parts and accessory parts of breathing masks, such as, for example, filters or breathing valves. As breathing apparatuses or their component parts as a rule are safety-related devices, during cleaning of said devices several requirements are to be observed. Along with sufficient cleaning and sterilization, it must be observed in many cases that accessory parts have to remain associated with the respective breathing masks for technical reasons. In addition, as a rule, it is also a requirement that gas-conducting regions of certain elements of breathing apparatuses, for example gas-conducting regions of breathing valves, must not come into contact with cleaning fluid, for example not with water and/or cleaning solution.

In many cases, breathing apparatuses, such as for example breathing masks and the accessories thereof, are either cleaned by hand or washed in modified washing machines by means of protective bags and/or by means of adapters. The cleaning of sensitive structural elements of the breathing apparatuses, such as for example breathing valves, in many cases is effected by hand. Where applicable, manual cleaning can be supported by placing in ultrasound cleaning devices.

Most of the known methods and devices for cleaning breathing apparatuses, such as, for example, breathing masks, in particular protective breathing masks, and the accessory parts thereof, comprise a plurality of disadvantages. Thus, manual cleaning of the breathing apparatuses is very labor-intensive. In addition, the cleaning process in this case is strongly influenced by the individual cleaning force and as a result can hardly be standardized.

EP 0 935 687 B1 makes known in general a washing machine which comprises a lye container with a drum. An outer surface of the drum comprises a curved structure directed toward the drum interior, holes being arranged in its corners on edge contours of the curvature directed toward the drum exterior. Particularly gentle cleaning of equipment items for rescue teams is possible in principle using these types of washing machines.

Cleaning in modified laundry washing machines is, however, equally comparatively time-intensive in practice. In addition, the breathing apparatuses or the component parts thereof are in many cases filled with cleaning fluid in the interior after cleaning, as they are either arranged randomly in the drum of the washing machine or as their position inside the drum is fixed and cannot be influenced in a targeted manner such that, as a result, the breathing apparatuses cannot drain when the cleaning procedure ends. Accessory parts cannot be cleaned for the most part in the washing machine at the same time as individual association is frequently lost during the process.

In addition, washing machines in which ventilation hoses can be washed are known from the medical environment. These types of washing machines are, as a rule, developed as single-circuit machines, also designated as water change machines. This means that the washing machines comprise a washing container in which the cleaning and the conditioning of the cleaning fluid are effected. For the change in a cleaning fluid, for example for a change from a washing solution to a rinsing liquid, a total water change inside the container is necessary.

Particularly critical in the case of the known methods and devices is the cleaning of gas-conducting elements of the breathing apparatuses such as, for example, one or several tubes, hoses or valves and/or breathing valves. To date there are only a few automated cleaning methods available for these types of breathing valves which would satisfy the abovementioned safety requirements. The cleaning method made known from DE 10 2007 012 768 B4, in contrast, comprises the above-described disadvantages and is comparatively expensive. In addition, the device shown does not enable simultaneous cleaning and, where applicable, disinfection of breathing valves and protective breathing masks as well as accessory parts. Washers from the medical environment which have been adapted for mask cleaning are not suitable for cleaning and sufficiently sterilizing breathing valves.

EP 1 088 928 A1 makes known a holding system for protective breathing masks in a laundry treatment machine. The holding system comprises a carrying bracket which is arranged so as to rotate at the same time in a drum of the laundry treatment machine and to which the protective breathing masks can be connected.

DE 200 03 743 U1 and DE 298 22 172 U1 each make known devices for treating protective suits. Clothes hangers which include flexible air outlet nozzles are used in this case. The clothes hangers are each fastened on a pivot device. Cleaning of breathing apparatuses by means of the devices shown is generally not possible or only possible with difficulty.

DE 11 74 169 B discloses a device for cleaning protective breathing masks. A rotatably mounted tubular framework where the masks to be cleaned are clamped on holders is provided in a housing in this case. By means of the rotary framework, the protective breathing masks are moved with a rotating movement through a bath of cleaning liquid in a tub.

DE 10 2007 012 768 B4, however, makes known a method and a device for cleaning breathing valves. In this case, the items to be cleaned are fitted onto holders of a rotating element and are repeatedly immersed into a liquid bath with cleaning liquid, disinfecting liquid and rinsing liquid. In this case, breathing valves initially have compressed air applied to them between the valve and the tube connection for sealing and are then immersed into the liquid bath. However, a disadvantage of such types of immersion methods is that complex holders with corresponding actuators are necessary in order to ensure that cleaning fluid is removed from the various cavities after cleaning as a result of corresponding movements.

U.S. Pat. No. 3,881,503 A describes a device for washing and decontaminating anesthesia equipment items. In this case, among other things, a nozzle system is provided, by means of which highly pressurized water jets can be sprayed onto the items to be cleaned.

DE 100 20 835 A1 makes known a device for treating protective breathing masks. This provides a receiving means which is to be fitted with protective breathing masks, where the protective breathing masks are coupled to the receiving means by means of the breathing apparatus connection. It additionally describes that a collecting device for collecting treatment means as well as a pump for supplying the treatment means are provided in a booth of the device.

DE 2 131 055 describes a washing apparatus for hollow items, having a tub and a drive shaft inserted into the tub. In addition, a holding device is provided by means of which several hollow items to be washed can be moved by the shaft. It is additionally provided that different types of baskets (for example an anesthetic basket 42 or an inhalation basket 195) can be moved into the washing chamber.

DE 10 2005 033 618 B3 makes known a device for cleaning protective breathing masks. The device comprises a closable housing and at least one receiving means for at least one protective breathing mask that is arranged in a carrier. Additionally provided are a nozzle arrangement and a brush arrangement, the protective breathing masks being brushed as a result of a movement of the protective breathing masks. However, individual assignment and cleaning of the accessory parts of the masks is not possible by means of the disclosed device. In addition, the cleaning of gas-conducting elements, such as for example breathing valves, is not possible using the disclosed device. DE 200 03 744 U1 also makes known a device for cleaning, disinfecting and drying protective breathing masks which comprises a carrying framework with an assigned nozzle system and individual treatment locations. This device is not suitable either, in principle, for cleaning gas-conducting elements and accessory parts.

DE 10 2007 009 936 A1 makes known a cleaning apparatus for compressed air breathing apparatuses. This device comprises a receiving chamber that is delimited by a protective grid and rotating nozzle carriers. The nozzle carriers are in this case situated outside the protective grid. However, a disadvantage of the device shown is that cleaning liquid can penetrate into gas-conducting regions.

WO 2011/144518A2 makes known a cleaning device for cleaning breathing apparatuses, in particular breathing valves and/or breathing masks. The cleaning device includes at least one cleaning chamber for receiving at least one breathing apparatus. The cleaning device additionally comprises at least one fluid device for applying at least one cleaning fluid to the breathing apparatus. The cleaning device additionally comprises at least one pressurizing device with at least one pressure connection. The pressure connection is connectable to at least one gas-conducting element of the breathing apparatus. The pressurizing device is set up to apply pressurized gas to the gas-conducting element. In addition, a holder for receiving breathing apparatuses is described which can be developed in particular in such a manner that accessories of the breathing apparatuses remain associated in each case with a breathing apparatus. The holder can include a basket-like receptacle in which the accessories are received.

In spite of the advantages obtained with the known methods and devices, in particular within the framework of automated cleaning of breathing apparatuses, there is still a considerable need for improvement in practice. In particular with regard to the known holders which receive the breathing apparatus or parts of the same during the cleaning operation, it can be ascertained in many cases that said holders are comparatively non-specific for the breathing apparatus used in each case. Thus, in practice, in many cases universal holders are used, for example in the form of baskets or other load carriers, in which the numerous component parts of the breathing apparatus are received in many cases in a disorderly and unaligned manner. Accordingly, in many cases a cleaning or disinfection result may not be optimum and can be highly variable.

OBJECT OF THE INVENTION

It is accordingly an object of the present invention to provide devices and methods for cleaning breathing apparatuses which avoid the disadvantages of known devices and methods at least extensively. In particular, reliable cleaning and, as an option, reliable sterilization or even disinfection of the different component parts, formed in various ways, of the breathing apparatuses is to be made possible, which cleaning comprises a high degree of reproducibility with regard to the result.

DISCLOSURE OF THE INVENTION

Said object is achieved by the devices and the method with the features of the independent claims. Advantageous further developments of the invention, which are realizable individually or in combination, are shown in the dependent claims.

Here and below, the terms "have", "comprise", "incorporate", "include" or "contain" as well as arbitrary grammatical variations of said terms are used in a non-exhaustive manner. Accordingly, said terms can relate both to a situation in which, apart from the features which are introduced by said terms, no further features are provided and to a situation in which one or several further features are present. For example, the statement "A comprises B" can relate both to the situation in which A comprises no further features along with feature B and to the situation in which A includes one or several further features along with the feature B, for example a feature C, features C and D or even further features.

In a first aspect of the present invention, a product range for cleaning breathing apparatuses is proposed which includes at least two holders. A product range, frequently also designated as a kit, is generally to be understood within the framework of the present invention as a plurality of objects which can be handled completely or in part independently from one another and which can support or supplement one another in their functions.

The product range serves for cleaning and as an option additionally also for disinfecting breathing apparatuses. Breathing apparatuses in this case are generally to be understood as devices which are set up to provide breathing gas to at least one human and/or animal user in any way possible. Reference can be made to the above description, for example, for possible applications. Said breathing apparatuses can be complete, operationally-ready breathing apparatuses or also component parts of the same such that below no difference is made conceptually between breathing apparatuses and the component parts thereof. In particular, the breathing apparatuses, as is given in more detail below, can include one or several breathing masks, in particular protective breathing masks, one or several hoses, one or several valves, one or several filters, one or several pressurized gas containers, one or several breathing valves, one or several pressurized gas cylinders, one or several carrying frameworks for pressurized gas cylinders or also in principle arbitrary combinations of the named and/or other elements.

The product range includes a plurality of holders. In this case at least two holders are provided, namely at least one first holder and at least one second holder, the intended purposes and developments of which are described in more detail below. One or several further holders can be provided alongside which are also described in more detail below.

The product range and in particular the holders of the same include at least one first holder for cleaning breathing masks and breathing valves. Said first holder includes at least one mask holding device for positioning at least one breathing mask. In general, in this case, positioning within the framework of the present invention is to be understood as an object being held in a directed manner such that, after positioning, the object comprises a defined position and/or a defined spatial alignment, at least within the framework of predetermined tolerances.

The first holder additionally comprises at least one breathing valve holding device for positioning at least one breathing valve and at least one pressurizing device with at least one pressure connection. The pressure connection is connectable to the breathing valve, and the pressurizing device is set up to apply pressurized gas to the breathing valve during cleaning.

The product range and in particular the holders of the same additionally include at least one second holder for cleaning carrying frameworks for pressurized gas cylinders for breathing apparatuses. In general, in this case, a carrying framework is to be understood as a framework which can be fitted onto the back of a user and by means of one or several carrying belts, which can be component parts of the carrying framework or also separate components, can be secured to the back of the user. The carrying belts can include one or several shoulder straps, for example, and/or one or several waist belts. As an alternative to one or several carrying belts or in addition to them, the carrying belts can also be developed in the form of a jacket by means of which the carrying framework can be secured on the back of the user. The pressurized gas cylinders can include, for example, pressurized gas cylinders with breathing air and/or an oxygen mixture. The second holder includes at least one carrying framework holding device for positioning at least one carrying framework.

The product range, in this case, is generally developed in such a manner that the holders are dimensioned in such a manner that they can be moved into a cleaning apparatus for cleaning the breathing apparatuses so as to be exchangeable. Thus, the first holder and/or the second holder can be used selectively and/or, as an option, at least one further holder. Said dimensioning can be effected, for example, in such a manner that the holders, for example the first holder and the second holder as well as, as an option, at least one further holder, comprise an area that is identical at least within the framework of component tolerances and/or identical exterior dimensions. As provided in more detail below, this can be effected in particular as a result of the first holder and the second holder, and where applicable, as an option, possible further holders, being able to comprise a basic basket that is structurally the same and/or identical, onto which in each case different sets are fitted or can be fitted.

The mask holding device can in particular include a framework. Said framework can comprise in particular at least one holding bracket for the at least one breathing mask, wherein the breathing mask can be put over the holding bracket. As a result of putting the breathing mask over the bracket, the holding bracket can penetrate, for example completely or in part, into an interior of the breathing mask. The holding bracket can be set up in particular in such a manner that the breathing mask can be put over the holding bracket in such a manner that an inside surface of the breathing mask points upward. The term "upward", in this case, is to be understood as a spatial direction which, in a state in which the first holder is moved into a cleaning chamber of the cleaning apparatus, points spatially upward. In this way, cleaning fluid can be applied in particular from above to the inside surface of the breathing mask, which is frequently strongly loaded by sweat or saliva in use. At the same time, the inside surface should be positioned in such a manner in this case that it is at an angle to the horizontal so that cleaning fluid is able to drain off downward out of said inside surface of the breathing mask. The mask holding device can be developed in a corresponding manner.

The framework of the mask holding device can be in particular a wire framework. The holding bracket can include in particular a wire bracket, in particular a wire bracket that is bent in a U-shaped manner.

The framework can in particular additionally comprise at least one further holding bracket for at least one inner mask of the breathing mask. Thus, in the case of many breathing masks, an inner mask which can lie for example tightly over the nose and/or mouth of the user, is additionally provided inside an outer mask. In the bottom region, said inner mask typically has an opening which can be connected, for example, directly to a breathe-out opening of the breathing mask. As a result of said realization the breathing mask, in particular the protective breathing mask, can be divided into an inner and an outer region. On its side regions the inner mask typically comprises one or several non-return valves which allow an air flow into the interior. As a result, a flow of fresh air can be effected from the pressurized gas cylinder, for example the compressed air cylinder, by means of a breathing valve into the outer region of the breathing mask and by means of the named non-return valves into the inner mask. As a result of said design, moist, exhaled air is able to be prevented from penetrating into the outer region of the breathing mask, and one or several viewing windows can be prevented from steaming up, for example. This fact can be taken into account by providing at least one holding bracket for at least one inside mask in the first holder.

The at least one further holding bracket for the at least one inner mask can also be developed as a wire bracket.

The mask holding device can comprise, as an option, one or several fixing elements for fixing the at least one breathing mask and/or the at least one optional inner mask. Said fixing elements can comprise in each case, for example, an open position and a closed position. In the open position, the respective breathing mask and/or optional inner mask can be moved, for example, into the mask holding device and/or the respective breathing mask and/or optional inner mask can be removed, for example, out of the mask holding device. In the closed position, for example the respective breathing mask and/or optional inner mask can be fixed to prevent slipping during a cleaning operation, for example. The at least one optional fixing element can be mounted, for example, so as to be movable. For example, this can include a wire bracket and/or wire ring. For example, in each case one fixing element for one inner mask can be pushed movably onto a wire bracket and/or another holder of an associated breathing mask. Other developments are, however, also conceivable, for example pivotable embodiments and/or embodiments that are displaceable in another manner.

Further possible developments relate to the breathing valve holding device. Thus, said breathing valve holding device can comprise, for example, at least one receiving means into which a connecting piece of the breathing valve is pluggable and in which the connecting piece is held in a fixed manner once it has been plugged in. For example, said receiving means can include a round opening. The receiving means can include, for example, a seal, into which the connecting piece of the breathing valve can be plugged. Thus the receiving means can include, for example, at least one friction brake for holding the breathing valve in a friction locking manner. Said friction brake can be realized, for example, in the form of at least one rubber ring and/or at least one sealing ring into which the connecting piece can be plugged and can be held in a friction locking manner.

The abovementioned pressure connection can comprise, in particular, at least one coupling for coupling on a pressurized gas hose of the breathing valve. Standardized couplings can be used in this connection, for example. The coupling can also comprise, for example, at least one adapter for coupling on several different types of pressurized gas hoses.

The coupling can be closable in particular by at least one removable cap when no pressurized gas hose is connected. For example, the removable cap can be a metal cap and/or a plastics material cap, for example an elastomer cap. The cap can be connected to the pressure connection, for example by means of a flexible locking web such that losing said cap even when it has been removed is prevented.

The pressurizing device can comprise, for example, at least one compressed air supply. The compressed air supply can open out in particular into a pressurized gas line, wherein the pressure connection can be fitted onto the pressurized gas line. The pressurized gas supply can include in particular at least one hose.

The optional pressurized gas line can be developed in particular as a carrying component of the first holder and can carry, for example, at least the breathing valve holding device. A rigid component, which is at least dimensionally stable in this respect such that it does not alter its form at least macroscopically when loaded by the breathing apparatus or parts of the same, is designated in this case within the framework of the present invention as the carrying component.

Thus, the pressurized gas line can be developed in particular as a frame. Said frame can be, for example, a rectangular frame. The frame can be developed in particular in a ring-shaped manner, in particular can be closed in a ring-shaped manner. Thus, said frame can be, for example, a tubular frame which is developed in a ring-shaped manner, in particular is closed in a ring-shaped manner and which can comprise, for example, a rectangular cross section. In this way pressure can be applied uniformly in a ring-shaped manner, for example, inside the pressurized gas line.

The development of the pressurized gas line as a frame is particularly advantageous in conjunction with a development where several holders share a common basic basket, onto which in each case holder-specific sets can be fitted in a selective manner. Thus, as provided in even more detail below, the product range can comprise several holders, the holders comprising in each case one basic basket and in each case at least one set, the basic basket of the holders being structurally the same and consequently exchangeable for example between the holders. Thus, for example, the same basic basket can be usable in a selective manner for the at least two different holders.

The sets of the holders can then be developed, for example, differently. Thus, for example, the first holder can comprise a first set which can be fitted onto the basic basket, and the second holder can comprise a second set which can also be fitted onto the basic basket. Further holders can comprise further sets in a corresponding manner.

For example, the first set can comprise the abovementioned pressurizing device with the at least one compressed air supply which opens out into the at least one pressurized gas line, the pressure connection preferably being fitted onto the pressurized gas line. The pressurized gas line can be developed as the carrying component of the first set and can carry in particular at least the breathing valve holding device. The pressurized gas line can be developed as a frame, in particular as a closed frame.

Thus, the frame formed by the pressurized gas line can lend the necessary stability, for example, to the first set. Thus, a user, when changing the sets, is able to grip, for example, the first set at the frame and remove it from the basic basket or place it onto the basic basket. The frame can therefore improve the handling ability and the stability of the product range in a considerable manner. The frame can also comprise one or several handles, as an option, in order to facilitate removing the first set from the basic basket or placing it onto the basic basket. In addition, the frame can be developed in such a manner that all the component parts of the first holder, with the exception of the basic basket, are connected or connectable directly or indirectly to the frame such that, for example, as a result of removing the frame from the basic basket, all the component parts of the first set are removable from the basic basket or as a result of placing the frame onto the basic basket all the component parts of the first set can be fitted onto the basic basket. The pressurizing device can therefore serve for at least one dual function where, on the one hand, pressurizing is ensured and where, on the other hand, the stability and handling ability of the product range are improved in a considerable manner.

The first holder can be set up in particular to receive a plurality of breathing masks and a plurality of breathing valves and can comprise accordingly a plurality of mask holding devices and a plurality of breathing valve holding devices as well as a plurality of pressure connections. In particular, in this case, the mask holding devices and the breathing valve holding devices, when viewed along a periphery of the first holder, can be arranged in an alternating manner. Said alternating arrangement can make possible in particular an easier association between the breathing masks and the breathing valves such that protection against mix-ups can be ensured at least extensively.

The first holder can additionally comprise at least one small parts basket. A small parts basket is to be understood in this case in general within the framework of the present invention as a device with at least one interior for receiving small parts of the breathing apparatuses, the interior being at least extensively closed. Said small parts basket can be developed, for example, in the form of a cuboid. For example, at its top end the small parts basket can comprise an opening through which the small parts can be inserted into the interior of the small parts basket. Said opening can be closed or can be closable, for example, by one or several covers.

The small parts basket can comprise in particular a plurality of openings, that is openings in at least one wall of the small parts basket, preferably in all the walls of the small parts basket which surround an interior of the small parts basket. Cleaning fluid, in particular, is able to penetrate into the interior of the cleaning basket through said openings. Said openings can comprise in particular an equivalence diameter of between 3 mm and 20 mm, in particular of between 5 mm and 15 mm and in a particularly preferred manner of 10 mm. Said opening widths, for example mesh apertures, have proved to be particularly advantageous for cleaning accessory parts of breathing apparatuses, as in this way, on the one hand, sufficient cleaning fluid is able to penetrate into the interior of the small parts basket in order to clean the small parts sufficiently and as, on the other hand, the small parts are not able to fall out of the interior through the openings.

The small parts basket can be produced in particular totally or in part from a wire mesh. As an alternative to this or in addition to it, however, other materials can also be used, for example plastic materials, for example a plastics material mesh. A metal small parts basket, for example a sheet metal basket, is also conceivable in principle.

The small parts basket can be removable, for example, from the first holder. Thus, the first holder can comprise, for example, at least one receiving means for insertion of the small parts basket. For example, the first holder can comprise a wire framework in which one or several openings for the at least one small parts basket are provided.

It is particularly preferred when a plurality of small parts baskets is provided. The small parts baskets can be closable, in particular by means of one common cover. The first holder can be set up, for example, for cleaning a plurality of breathing masks and a plurality of breathing valves, wherein each pair consisting of one breathing mask and one breathing valve can have assigned thereto in each case one small parts basket. For example, the above-described receiving means for insertion of the small parts baskets can be developed in such a manner that a pair, consisting of one breathing mask and one breathing valve, is always assigned a certain small parts basket. Protection against a mix-up is once again ensured in this manner.

Further possible developments relate to the carrying frame holding device. Thus, the carrying frame holding device can comprise, for example, at least one support which projects upward from the second holder. Said support can project upward in particular in a substantially vertical manner. In this case, deviations from a totally vertical orientation are also conceivable, for example by no more than 20°, in particular by no more than 10°. The support can include in particular a flat plate. The flat plate can also comprise, for example, a plurality of openings. As a result of said openings, it can be ensured, for example, that cleaning fluid is able to pass from a rear side of the plate, which points away from the carrying framework, toward the carrying framework. For example, said plate can be produced from a metal material and/or from a plastics material. Thus, for example, the plate can be produced at least in part from a wire mesh. As an alternative to this or in addition to it, once again other alternatives are conceivable, for example a plastics material mesh with a plurality of openings and/or a perforated metal plate with a plurality of openings. Generally speaking, it is once again particularly preferred when the openings comprise an equivalence diameter of between 3 mm and 20 mm, preferably an equivalence diameter of between 5 mm and 15 mm and in a particularly preferred manner an equivalence diameter of 10 mm.

The second holder can additionally comprise in particular at least one frame. The support can be connected to said frame by a plurality of cross struts and can be stabilized thereby. Thus, for example, during cleaning of at least one carrying framework, the frame can be received substantially horizontally inside a cleaning chamber of a cleaning apparatus, whilst the support is arranged substantially vertically with respect to said frame and is connected to the frame and stabilized by it as a result of the plurality of cross struts. It can be ensured for example in this manner that the frame is not considerably deformed by the heavy carrying framework.

As an alternative to the at least one support or in addition to it, the carrying framework can also comprise one or several other elements which can hold and/or support and/or fix the carrying frame. Thus, the carrying framework holding device can also comprise, for example, one or several fixing elements for the total or partial fixing of at least one carrying framework. For example, the carrying framework holding device can comprise at least one suspending means, on which or by means of which at least one carrying framework or at least one part of the same is able to be suspended.

As stated above, the product range can include further holders along with the named at least one first holder and the at least one second holder. Thus, the product range can additionally comprise, for example, at least one third holder for cleaning breathing valves. The third holder can comprise for example at least one breathing valve holding device for positioning at least one breathing valve. The third holder can additionally comprise in particular at least one pressurizing device with at least one pressure connection, wherein the pressure connection can be connectable to the breathing valve and wherein the pressurizing device can be set up to apply pressurized gas to the breathing valves during cleaning. The third holder can be developed in particular in such a manner that it does not have a mask holding device.

Further possible developments relate to the development of the third holder. Thus, with reference to the breathing valve holding device with regard to possible optional developments reference can be made extensively to the above description of the first holder and there to the features of the breathing valve holding device. Thus, the breathing valve holding device of the third holder can once again comprise, for example, at least one receiving means in which a connecting piece of the breathing valve is pluggable and in which the connecting piece is held in a fixed position after being plugged in. The receiving means can once again include a friction brake for holding the breathing apparatus in a friction locking manner.

The pressure connection of the third holder can once again comprise, in particular, at least one coupling for coupling on a pressurized gas hose of the breathing valve. The coupling can once again be closable in particular by at least one removable cap when no pressurized gas hose is connected. The pressurizing device of the third holder can once again comprise, in particular, at least one compressed air supply, it being possible for the compressed air supply to open out, for example, into a pressurized gas line of the third holder, it being possible for the pressure connection to be fitted onto the pressurized gas line. The pressurized gas supply can include in particular at least one hose. The pressurized gas line can once again be developed in particular as a carrying component and carry at least the breathing valve holding device. The pressurized gas line can once again be developed in particular as a frame. The frame can once again be closed in particular in a ring-shaped manner.

The third holder can also be set up in particular in order to receive a plurality of breathing valves. As also in the case of the first holder, it is particularly preferred in the case of the third holder when at least two, preferably at least four and in a particularly preferred manner at least eight breathing valves can be received.

The third holder can also once again comprise at least one small parts basket. With reference to possible developments of the small parts basket, reference can once again be made to the above description of the first holder. The small parts basket can once again be set up in particular to receive accessory parts during a cleaning operation. The small parts basket can once again comprise a plurality of openings, for example openings with an equivalence diameter of between 3 mm and 20 mm, in particular of between 5 mm and 15 mm and in a particularly preferred manner of 10 mm. The small parts basket can once again be produced in particular totally or in part from a wire mesh. The small parts basket can additionally once again be removable in particular from the third holder. Thus, the third holder can comprise, for example, at least one receiving means for insertion of the small parts basket, it being possible for the receiving means, as also in the case of the first holder, to be developed for example in such a manner that the insertion of the small parts basket can be effected in a reversible manner.

Once again a plurality of small parts baskets can also be provided in the case of the third holder. The plurality of small parts baskets can once again be closable for example by a common cover.

The third holder can be set up, as stated above, in particular for cleaning a plurality of breathing valves. Each breathing valve, in this case, can have assigned thereto in each case one small parts basket. Thus, for example, the at least one receiving means can once again be developed in such a manner for insertion of the at least one small parts basket that in each case one small parts basket is assigned spatially to a certain breathing valve holding device such that a clear assignment can be ensured. Prevention against a mix-up can also be ensured once again in this way.

As an alternative to or in addition to the third holder, the product range can additionally comprise at least one fourth holder for cleaning breathing masks. Said fourth holder can once again comprise in particular at least one mask holding device for positioning at least one breathing mask. It is particularly preferred in the case of said fourth holder when the fourth holder does not comprise a breathing valve holding device. With reference to possible developments of the mask holding device, reference can once again be made extensively to the above description of the first holder. Other developments, however, are also possible in principle.

Thus the mask holding device of the fourth holder can once again include, for example, at least one framework, it being possible for the framework once again to include for example at least one holding bracket for the at least one breathing mask, it being possible for the breathing mask to be put over the holding bracket. The holding bracket can once again be set up in particular in such a manner that the breathing mask can be put over the holding bracket in such a manner that an inside surface of the breathing mask points upward, for example upward in an angled manner. The framework can once again be a wire framework for example or can at least include a wire framework. The holding bracket can once again accordingly include, for example, at least one wire bracket.

The framework of the fourth holder can once again comprise for example at least one further holding bracket for at least one inner mask.

Analogously to the first holder, the mask holding device of the fourth holder can also comprise, as an option, one or several fixing elements for fixing the at least one breathing mask and/or the at least one optional inner mask. Said fixing elements can comprise in each case, for example, an open position and a closed position. In the open position, the respective breathing mask and/or optional inner mask can be moved, for example, into the mask holding device and/or the respective breathing mask and/or optional inner mask can be removed, for example, out of the mask holding device. In the closed position, for example the respective breathing mask and/or optional inner mask can be fixed to prevent slipping during a cleaning operation, for example. The at least one optional fixing element can be mounted, for example, so as to be movable. For example, this can include a wire bracket and/or wire ring. For example, in each case one fixing element for one inner mask can be pushed movably onto a wire bracket and/or another holder of an associate breathing mask. Other developments are, however, also conceivable, for example pivotable embodiments and/or embodiments that are displaceable in another manner.

The fourth holder can once again comprise, as also the first holder and the optional third holder, at least one small parts basket for receiving accessory parts during a cleaning operation. With reference to possible developments of the small parts basket, reference can once again be made for example to the above description. Other developments are, however, also possible in principle. Thus, the small parts basket can once again comprise for example a plurality of openings, for example openings in one, several or all walls of the small parts basket, it being possible for cleaning fluid to penetrate through said openings into the interior of the small parts basket. The openings can comprise for example an equivalence diameter of between 3 mm and 20 mm, in particular of between 5 mm and 15 mm and in a particularly preferred manner of 10 mm. Other dimensioning is, however, also possible in principle. As also in the case of the small parts basket of the first holder and/or of the small parts basket of the third holder, the openings can comprise an arbitrary cross section in principle, for example a round cross section and/or a rectangular cross section, for example a square cross section. The small parts basket can once again be produced, for example, entirely or in part from a wire mesh, other materials, however, once again as in the case above, also being usable.

The small parts basket can once again be removable in particular from the first holder. Thus, for example, the fourth holder can once again comprise for example at least one receiving means for the insertion of the small parts basket, for example a receiving means in a framework of the fourth holder. The fourth holder can once again comprise for example a plurality of small parts baskets. Said plurality of small parts baskets can once again be closable by a common cover.

The fourth holder can be set up in particular for cleaning a plurality of breathing masks, it being possible for each breathing mask once again to have associated therewith for example one small parts basket. For example, this can once again be effected as a result of a plurality of mask holding devices being provided, the receiving means being set up in such a manner that in each case one small parts basket is assigned spatially to one mask holding device. Protection against a mix-up can once again be ensured in this manner.

A further possible aspect relates to the holders. Thus, the different holders, that is the first holder and the second holder as well as additionally, as an option, the third holder and/or the fourth holder, are developed in such a manner that with, regard to one or several components, they are structurally the same or even have the same component parts, in the latter case for example a component part being exchangeable between the holders.

In particular the holders can comprise in each case at least one basic basket and at least one set. Thus, the basic basket of the holders, that is of the first holder and of the second holder as well as optionally of the third holder and/or of the fourth holder, can be structurally the same or even, as is described in more detail below, identical and exchangeable between the holders. In this case, however, the sets of the holders do differ from one another such that, for example, the first holder comprises a first set, the second holder a second set as well as optionally the optional third holder comprises a third set and/or optionally the optional fourth holder comprises a fourth set. In this case, the first set can differ from the second set. In addition, the first set and/or the second set can differ in each case from the third set and/or the fourth set.

A basic basket, in this case, is generally to be understood within the framework of the present invention as a basket which closes off the respective holder at the bottom and onto which the respective set can be fitted entirely or in part and/or into which the respective set can be moved entirely or in part. As is described in more detail below, the basket can comprise in particular a bottom part with a bottom surface as well as basket walls which extend upward from the bottom part. The bottom part and the basket walls together form a basket wall. Said basket wall can comprise, as explained in more detail below, in particular a plurality of openings.

A set is accordingly to be understood as a functional component which can be fitted onto the basic basket and/or can be moved entirely or in part into the basic basket and which is connected or can be connected in a reversible manner and/or permanently to the basic basket. Said functional component can in each case comprise for example one or several functional elements, such as, for example, the above-described mask holding device and/or the above-described breathing valve holding device and/or the above-named pressure connection and/or the carrying framework holding device and/or others of the named functional elements.

As stated above, the basic basket can comprise for example at least one bottom part. Generally speaking, the basic basket, for example the bottom part, can comprise a rectangular bottom area. The basic basket can additionally comprise an edge which points upward from said bottom part, for example an edge which stands upward at right angles from the bottom part. The bottom part can be developed for example in a flat manner and can be developed in such a manner that it is aligned horizontally when the basic basket is received in a cleaning chamber. The upwardly pointing edge, which is preferably a circumferential edge, can be accordingly arranged for example substantially vertically when the basic basket is received with the respective holder in the cleaning chamber.

The sets can then be fitted, for example, in each case on the edge of the associated basic basket. The sets can generally be connectable to the associated basic basket, for example in each case in a reversible manner. For example, the sets can be connectable in a reversible manner to the edge of the basic basket. As an alternative to this, however, a fixed connection is also possible in principle.

A non-positive locking connection is possible, in particular, for the purpose of producing a reversible connection. Thus, the sets can be connected or be connectable to the associated basic basket for example in each case as a result of a non-positive locking connection by means of at least one connecting element, which can be a component part of the respective set and/or of the basic basket. For example, said non-positive connection can include a latching connection. However, as an alternative to this or in addition to it, other types of connection and/or combinations thereof can also be used in principle.

As stated above, it is particularly preferred when, with regard to at least one component, the holders have the same components, or even at least one component can be used identically in all the holders. This can be in particular the named basic basket. Thus, in particular the same basic basket can be a component part of the holders, the holders being differentiable in their sets which are connectable to said basic basket in a reversible manner. Thus, for example, different sets can be fitted onto the same basic basket one after another in different cleaning steps. In principle, however, a development is also possible where different holders comprise different basic baskets even when said basic baskets can be basically structurally the same.

As stated above, the basic basket can comprise in particular a flat bottom part. In addition, the basic basket can comprise an edge, preferably a circumferential edge.

The basic basket can be produced in particular entirely or in part from at least one material selected from the group consisting of a metal, a wire material and a plastics material. Other materials can also be used in principle. If a metal is used, this can be in particular a wire-shaped metal. As an alternative to this or in addition to it, however, metal sheets can also be used.

The basic basket can comprise, as stated above, in particular a plurality of openings. Said openings can make it possible for cleaning fluid to be applied from below onto the breathing apparatus received in the respective holder and/or can make it possible for the cleaning fluid to drain away downward once the breathing apparatus has been acted upon. Said openings can have an arbitrary cross section in principle, for example a round and/or polygonal, in particular a rectangular cross section. For example, the basic basket can be developed entirely or in part as a grid-like basket. The openings can preferably comprise in general an equivalence diameter of between 3 mm and 20 mm, in particular an equivalence diameter of between 5 mm and 15 mm and in a particularly preferred manner an equivalence diameter of 10 mm.

The basic basket can comprise in particular a mesh. In particular, the basic basket can be produced at least in part from a wire grid. When the basic basket comprises a bottom part as well as an edge, for example according to the above-described embodiment, both the bottom part and the edge of the basic basket can be produced at least in part from the wire grid. Other developments are, however, also possible in principle.

In a further aspect of the present invention, a cleaning system is proposed for cleaning breathing apparatuses, in particular breathing valves and/or breathing masks, for example protective breathing masks. The cleaning system includes at least one cleaning apparatus which comprises at least one cleaning chamber for receiving at least one breathing apparatus, wherein the cleaning apparatus additionally comprises at least one fluid device for applying at least one cleaning fluid to the breathing apparatus. In addition, the cleaning system comprises at least one product range according to the invention according to one or several of the above-described embodiments and/or according to one or several of the embodiments described in more detail below.

The cleaning system, in this case, is developed in such a manner that the holders of the product range are receivable in a selective manner in the cleaning chamber. Thus, the cleaning chamber can comprise, for example, at least one rail and/or one bearing surface and/or another type of receiving means into which the holders are insertable in a selective manner, preferably in a reversible manner. The cleaning apparatus is additionally set up to use the first holder in at least one cleaning step and to apply pressurized gas in said cleaning step by means of the pressure connection to at least one breathing valve which is received in the first holder.

With regard to possible developments of the cleaning apparatus, with the exception of the holders and/or the product range, reference can be made for example to WO 2011/144518, already mentioned above. Other developments are, however, also possible in principle.

Thus, the cleaning chamber can be developed in principle, for example, as a cleaning chamber that is closed, open or to be opened. It is particularly preferred when the cleaning chamber is surrounded on all sides or at least in two dimensions by a housing which can be developed totally closed and but which can also comprise, in principle, one or several feed-throughs. The cleaning chamber can be developed in particular as a rigid cleaning chamber, that is as a cleaning chamber which does not alter its position and/or alignment during a cleaning operation. As an alternative to this or in addition to it, the cleaning chamber can additionally, however, also be developed as a movable cleaning chamber, for example as a pivotable and/or rotatable cleaning chamber which alters its position and/or orientation in the cleaning apparatus during a cleaning operation, for example as a result of a turn, a rotation, a centrifuging operation, a vibrating operation or similar movements. In this respect the cleaning chamber can be developed for example as a wash chamber of a washer, and the cleaning apparatus can be developed as a washer, and/or the cleaning chamber can be developed as a drum of a washing machine and the cleaning apparatus can be developed in the form of a washing machine. For example, commercial-type or domestic dishwashers and/or laundry washing machines can be modified according to the invention.

The cleaning apparatus additionally comprises at least one fluid device for applying at least one washing fluid to the breathing apparatus. A cleaning fluid, in this case, is to be understood as a basically arbitrary liquid and/or a basically arbitrary gas which can have a macroscopically and/or microscopically cleaning effect on the breathing apparatus. A fluid device is generally be understood as a device, by means of which the cleaning fluid is able to be applied directly or indirectly in an arbitrary manner onto the breathing apparatus that is received inside the cleaning chamber. This can be effected, for example, in the form of a direct application, for example as a result of spraying, dripping, irradiating or a combination of the named and/or other direct types of application, where cleaning fluid emerging out of the fluid device directly contacts the breathing apparatus. Said development of the application can be effected in particular with a fixed cleaning chamber, for example with a washer. As an alternative to this or in addition to it, the application can also be effected by means of the fluid device in such a manner that the fluid device fills the cleaning chamber fully or in part with fluid such that items to be cleaned that have been received in the cleaning chamber come into contact with the cleaning fluid in at least one position of the cleaning chamber. Said development of the application can be utilized in particular where the cleaning chamber is developed as a movable cleaning chamber, for example in the form of a drum. Combinations of the named types of application and/or other types of application are also possible. Irrespective of whether the cleaning chamber is developed in a rigid or movable manner, the application with the cleaning fluid can be effected in simple mode by the cleaning fluid simply being applied once to the breathing apparatus. As an alternative to this or in addition to it, however, cleaning can also be effected in recirculation mode by cleaning fluid being applied onto the breathing apparatus multiple times. These types of recirculation modes and recirculation circuits are known, for example, from conventional dishwashers or washing machines.

The cleaning device, as stated above, is set up to use the first holder in at least one cleaning step and to apply pressurized gas by means of a pressure connection onto at least one breathing valve that is received in the first holder. For this purpose, the cleaning apparatus can comprise at least one apparatus-side pressurizing device which interacts with the pressurizing device of the first holder, for example by the pressurizing device on the apparatus side being connected to the pressurizing device of the first holder.

A pressurizing device is generally to be understood within the framework of the present invention as a device which is set up to be able to provide a pressurized gas, that is a gas at a pressure above normal pressure, for example a pressure of at least 1.5 bar, preferably a pressure of at least 2 bar. A pressure connection is to be understood in principle as an arbitrary connection of the pressurizing device by means of which the pressurized gas can be made available to the pressuring device.

The apparatus-side pressurizing device can be arranged in particular in the interior of the cleaning chamber and/or can be accessible from the interior of the cleaning chamber. Providing a plurality of pressure connections is also conceivable.

The pressurizing device of the first holder is to be developed in such a manner that the at least one pressure connection is connectable to the at least one breathing valve. In addition to the breathing valve, the pressurized gas, for example compressed air, nitrogen and/or a different pressurized gas, can be applied to one or several other gas-conducting elements in principle, by means of the pressurizing device. A gas-conducting element, in this case, is to be understood in general as an element to which a breathing gas is applied or which can come into contact with a breathing gas in another way when the breathing apparatus is utilized by a human or animal user. In particular, in this connection, this can be a breathing valve and/or a breathing hose with at least one valve. In particular, the gas-conducting element can be an element which comprises at least one hose and/or at least one other type of gas-conducting device with an interior and/or at least one valve, to which, as a rule, cleaning fluid must not be applied. For example, the gas-conducting element can be a region of the breathing apparatus to which a pressure above normal pressure is applied in operation, for example a gas-conducting region of a breathing apparatus above a normal pressure, for example above 1.5 bar, in particular above 2 bar.

The breathing valve can be, in principle, for example, a single-stage or also a multiple-stage breathing valve. For example, the pressurized gas can be applied onto part of a first stage and/or a second stage and/or, where applicable, further stages of the breathing valve, or even an entire breathing valve. For example, it can be applied onto at least one region between a hose connection and a valve of the breathing valve.

A connection between the pressure connection and the breathing valve is to be understood in general as a gas connection such that the pressurized gas can be transferred into the breathing valve, preferably without any loss of pressurized gas at said connection. Over and above this, the connection between the pressure connection and the breathing valve can include, as an option, at least one mechanical connection, in particular a positive locking and/or non-positive locking connection such that the breathing valve is able to be connected in a fixed manner to the pressure connection. For example, this can be a screw connection and/or a clamping connection and/or a tension connection, for which purpose the pressure connection and/or the breathing valve can in each case comprise at least one mechanical connecting element. In particular, this can be a plug connection in the form of a rapid-action coupling and/or a thread, for example a coupling part for a breathing connection of the breathing valve. A rapid-action coupling, in this case, is to be understood in general as a gas-tight and/or liquid-tight plug connection between two liquid-conducting components which can be secured mechanically as a result of a mechanical fixing means which can be produced and released in a simple manner, in particular without using a screw-type closure, for example by means of at least one tensioning hook and/or a bayonet closure and/or a screw-type closure, for example a cap nut. The connection can be producible in particular without tools. In particular, the pressure connection can include a plurality of adapters that are developed in a fixed or exchangeable manner for connecting to different types of breathing apparatuses. By means of said adapters, a plurality of different breathing valves can be connectable directly or indirectly to the pressure connection, for example different types and/or different models of breathing valves, for example of different manufacturers or producers. For example, an adapter set can be provided with a plurality of different coupling pieces (for example coupling pieces of a rapid-action coupling) and/or threads for connecting different breathing apparatuses. For example, these can be different rapid-action coupling systems and/or standard threads. As an alternative to this or in addition to it, the at least one pressure connection can also be developed, however, as a fixed pressure connection for a certain model of connecting element or for a certain model of gas-conducting element. It is particularly advantageous when the pressure connection and/or the coupling system are set up such that on the one hand no gas can be output when no counterpart is connected and that in this case no other medium, for example cleaning fluid, is able to enter the breathing valve either.

The optional apparatus-side pressurizing device of the cleaning apparatus is set up to apply pressurized gas onto the gas-conducting element in conjunction with the pressurizing device of the first holder as well as, where applicable, in a further cleaning step with the pressurizing device of the third holder. A pressurized gas, in this case, is to be understood in general as an arbitrary gas which comprises a pressure above normal pressure, that is a pressure above 1 bar. In particular, in this case this can be a pressure above 1.5 bar, in particular above 2 bar, and in a particularly preferred manner above 3 bar. In a particularly preferred manner, the pressurization with the pressurized gas is effected in such a manner that all the cleaning fluid is kept out of an interior of the breathing valve onto which pressurized gas is applied. The pressurized gas can be, for example, compressed air or another gaseous medium with an overpressure, for example nitrogen, carbon dioxide or similar. In particular, an insert gas can be used as pressurized gas.

The cleaning apparatus can be developed in particular in such a manner that the pressurization is effected by means of the pressurizing device during at least one cleaning operation, for example during at least one cleaning step or program step of a single-step or multiple-step cleaning program. In particular, the pressurized gas can be applied onto the breathing apparatus at the same time as the cleaning fluid is applied.

The cleaning apparatus can be developed in particular as a single-chamber washer and/or can include a single-chamber washer. A single-chamber washer, in this case, is to be understood as a washer with one single cleaning chamber in which several cleaning steps (also called program steps below) of a multiple-step cleaning program can preferably be carried out. Application inside a single-chamber washer can be effected in particular by a fluid device in the form of one or several nozzles, for example in the form of one or several spray nozzles and/or other nozzles, for example rigid and/or rotatable and/or pivotable nozzle arms. The single-chamber washer can be developed in particular as a so-called multi-circuit washer. Accordingly, the single-chamber washer can comprise for example at least one fluid tank which is realized separately from the cleaning chamber, it being possible to condition, for example to heat and/or act upon with additives, at least one cleaning fluid in the fluid tank independently of a cleaning process which is running in the cleaning apparatus. These types of washers with a multi-circuit principle are known from the area of industrial dishwashers, where, independently of the cleaning chamber, a tank is as a rule provided for conditioning a rinse liquid, for example a boiler and/or a tank with an instantaneous heater.

The pressurized gas can be provided by the cleaning apparatus itself and/or by an external device. Thus, the apparatus-side pressurizing device of the cleaning apparatus can comprise in particular at least one external pressure connection for connecting to an external pressure source. Said external pressure source can be a pressurized gas cylinder which is realized separately from the cleaning apparatus and/or a pressurized gas line on the building side, for example a compressed air line. As an alternative to this or in addition to it, the apparatus-side pressurizing device can also comprise at least one pressurized gas source integrated into the cleaning apparatus. In particular, at least one integrated pressurized gas cylinder can be provided and/or at least one integrated compressor, for providing the pressurized gas. As an alternative to providing one single pressurized gas or in addition to it, several pressurized gases can also be provided at the same time or one after another.

The cleaning apparatus can be set up in particular as a program automat in order to carry out a cleaning program with one or several program steps or cleaning steps. In particular, the cleaning apparatus can be set up to carry out a cleaning program with at least two different cleaning steps. For example, different types of cleaning fluids can be applied in different cleaning steps, for example at least one cleaning step in which a detergent solution is applied, and at least one further cleaning step, in particular a rinse step, in which a rinse fluid is applied. As an option, where applicable, at least one cleaning step which is developed as a drying step can also be provided, the drying, where applicable, being able to be effected in a passive manner, for example as a result of simple drip-drying, or, as an alternative to this, where the drying can also be actively supported, for example as a result of blowing out the breathing apparatuses automatically with compressed air and/or as a result of providing a heat source such as hot air, microwaves and/or at least one similar heat or drying source.

Further possible developments relate to the fluid device. As stated above, the fluid device can comprise in particular at least one nozzle. In particular, in this case this can be a nozzle which is selected from a spray nozzle, a wash nozzle, a spray arm, in particular a pivotable and/or rotatable spray arm, a nozzle that can be operated in recirculation mode. A combination of the named and/or other types of nozzles is also conceivable. As an alternative to this or in addition to it, the fluid device can also include, however, for example, a simple opening to allow the cleaning fluid to enter into the cleaning chamber.

The cleaning fluid can include in particular an aqueous cleaning fluid, that is water or water with the addition of one or several additives which can be present in dissolved form, in the form of an emulsion or also in the form of a suspension. As an alternative to this or in addition to it, the cleaning fluid can also include at least one detergent solution. A detergent solution in this case is to be understood in general as a solution of at least one surfactant in at least one solvent, for example also water. For example, this can be a commercial detergent which can also be used for dishwashers and/or which can be used in washing machines. However special detergent solutions can also be developed and/or used in principle. Once again as an alternative to this or in addition to it, the cleaning fluid can also include a cleaning fluid with at least one rinsing agent, that is an additive which facilitates the drying of the breathing apparatus and/or facilitates liquid drip-drying from at least one surface of the breathing apparatus. These types of rinsing agents, which can also include one or several surfactants, are known in principle from the area of dishwashing technology. Once again as an alternative to this or in addition to it, the cleaning fluid can also include at least one rinse fluid which in principle can be water, for example, and/or water with one or several additives. Once again as an alternative to this or in addition to it, the cleaning fluid can also include a cleaning fluid with at least one disinfecting agent, a disinfecting agent being able to be understood in principle as an arbitrary substance which comprises a germicidal action. These types of disinfecting agents are also known in principle from the prior art. Once again as an alternative to this or in addition to it, the cleaning fluid can also include demineralized water. As is stated in more detail below, the demineralized water can be provided for example in a corresponding demineralizing device of the cleaning apparatus, for example an ion exchanger. As an alternative to this or in addition to it, the demineralizing device can also include, however, for example, a reverse osmosis device. Once again as an alternative to this or in addition to it, the cleaning fluid can also include a heated cleaning fluid. These types of heated cleaning fluids are suitable in particular for rinsing, heated cleaning fluids being basically to be understood as cleaning fluids which are at a temperature of at least 25° C. Particularly preferred are temperatures of between 30° C. and 70° C. and in particular 60° C. Said temperatures have proved to be suitable in particular for cleaning flexible elastomer materials, as are frequently used for breathing apparatuses.

As shown above, high-quality cleaning fluids are particularly important for cleaning breathing apparatuses. In this way, for example microscopic or macroscopic contamination of the breathing apparatuses can be avoided. As a result of microscopic contamination such as, for example, mineral contamination, calcium deposits are created, for example, on vision surfaces such as for example vision windows of the breathing apparatuses. In addition, microbial contamination can result in contamination of the breathing apparatuses. It is, consequently, particularly preferred when the cleaning apparatus comprises at least one reverse osmosis device for preparing water, in particular demineralized water. A reverse osmosis device can be understood in general as a device which can prepare a fluid with a high degree of purity, using the principle of reverse osmosis. For example, the reverse osmosis device can comprise one or several osmosis diaphragms, through which clean constituents of the water can be pressed at high pressure such that a purified permeate is created, in contrast to which contaminants remain on a concentrate side. For example, pressures of above 2 bar, in particular above 5 bar, can be used in this connection.

As shown above, in particular commercially available laundry washing machines and/or dishwashers can be redesigned for the purposes of the present invention, for example industrial laundry washing machines and/or industrial dishwashers. Said redesigning can be effected in such a manner that the laundry washing machines or dishwashers are provided with an apparatus-side pressurizing device according to the above-described features. The cleaning apparatus can be developed, for example, as a front loading washer or as a cover-type washer. A front loading washer, in this case, is to be understood as a washer with a cleaning chamber which can be opened by a flap and/or a by a slide by a user standing in front of the washing machine. A cover-type washer is to be understood in this case as a washer, the cleaning chamber of which includes a cover, which can pivoted open and/or extended and which can be separated from other component parts of the cleaning chamber, for example from a base. These types of cover-type washers are known in principle from the area of industrial dishwasher technology. The cleaning chamber can be developed in particular in a rigid manner. The cleaning chamber can be developed so as to be lockable in general during the cleaning operation, in particular by providing an automatic locking means which is preferably activated during a program and can automatically be unlocked again after a program.

In a further aspect of the present invention, a method for cleaning breathing apparatuses is proposed. In the case of said method, the cleaning system according to the above description or according to the embodiments described in more detail below is used. The method comprises at least one first cleaning step and at least one second cleaning step. In the first cleaning step the first holder is used, wherein at least one breathing mask is moved into the mask holding device of the first holder. In this case, at least one breathing valve is moved into the breathing valve holding device. Pressurized gas is applied onto the breathing valve by means of the pressure connection, and the cleaning fluid is applied onto the breathing mask and the breathing valve the by means of the fluid device.

In the second cleaning step the second holder is used. In this case, at least one carrying framework for pressurized gas cylinders for breathing apparatuses is moved into the carrying framework holding device of the second holder. The cleaning fluid is applied onto the carrying framework by means of the fluid device.

For further possible details of the method, reference can be made in particular to the above description of the cleaning system.

The product range, the cleaning system and the method according to the present invention, in one or several of the above-described developments as well as, where applicable, in one or several of the developments described in more detail below, comprise numerous advantages in relation to known devices and methods of the named type. Thus, by means of the described product range, it is possible to realize a load carrier system which is able to receive breathing masks and their different component parts in such a manner that cleaning and/or disinfection is able to be carried out in an optimum manner. Individual parts of the breathing apparatuses which have to be disassembled for cleaning, are able to be received in such manner in the holders that they are able to be clearly assigned to the respective breathing masks and/or breathing valves.

Generally speaking, by means of the present invention it is possible to realize a flexible basket system which is especially matched to the cleaning of components around the breathing apparatuses. As stated above, the basket system can in each case include a basic basket and special sets which are releasably connected to the basic basket. As an option, integrated, assignable small parts containers can be provided in the form of small parts baskets, optionally with a cover, for example in the form of at least one cover grid.

The holders can be extremely versatile. Thus, they can be used, for example, for washing parts in a mask washer as well as also for subsequent drying in a drying cabinet. The optional basic basket can comprise, for example, a flat bottom part, for example produced from wire mesh. A lateral edging can also be produced from wire mesh. An opening width, for example a mesh width, of 10 mm has in this case proved to be very suitable in practice such that, on the one hand, the items to be cleaned can be reached in an optimum manner by nozzle jets and, on the other hand, loose component parts of the breathing apparatuses such as, for example, holding straps and/or strapping, cannot come into contact with the rotatable nozzle arms, which are optional and are extremely versatile in practice, and prevent their movement.

As stated above, different sets can be used with the basic basket which then, together with the basic basket, produce the respective holders. Thus, for example, a set can be provided for four breathing apparatuses and the individual parts thereof or for more than four masks, for example eight breathing masks, without breathing valves. Said set, together with the basic basket, can produce, for example, the above-described fourth holder. In addition, a combi-basket set can be provided, for example for four or more breathing masks as well as the individual parts thereof, with compressed air connections for four or more breathing valves. Said combi-basket set, together with the basic basket, can then produce for example the above-described first holder.

In addition, a basket set can be provided with compressed air connections for four, six, eight or more breathing valves. Said basket set can then produce, for example, together with the basic basket, the above-described third holder.

In addition, as stated above, a basket set for one carrying frame or a basket set for several carrying frames can be provided. Said basket set, together with the described basic basket, can then produce, for example, the above-mentioned second holder.

Small parts of the respective breathing masks and/or small parts of the respective breathing valves can be clearly assigned to one breathing mask and/or one breathing valve. Thus, for example, a clear assignment can be effected by means of the position of a small parts basket and/or a position of the holder.

The above-described sets can be realized advantageously in such a manner that they can also be fitted onto standard market baskets, which, where applicable, are already present in commercially available cleaning devices and/or drying cabinets. The basic baskets and basket sets can be produced in principle from arbitrary materials, for example from metal. Designs produced from plastics material and/or combined designs, however, are also conceivable.

As a result of the special realization of the product range of holders, all surfaces of the breathing apparatuses can be moistened very well by the cleaning fluid. The cleaning fluid can be recirculated and/or sprayed by nozzles, for example. The mechanical action of the nozzle jets can be supported by an optimum holder.

The cleaning fluid, for example the wash fluid, is able to drain unobstructed from all sides of the parts to be cleaned such that the contaminants are able to be removed entirely. As a result of the cleaning fluid draining well, a subsequent drying process can be made considerably easier and consequently also shortened. In practice this means, along with a time saving, better utilization of the drying cabinets and a saving in heating energy per breathing apparatus dried.

BRIEF DESCRIPTION OF THE FIGURES

Further details and features of the invention are produced from the following description of preferred exemplary embodiments, in particular in conjunction with the sub-claims. In this connection, the respective features can be realized individually on their own or in groups in combination with one another. The invention is not restricted to the exemplary embodiments. The exemplary embodiments are shown schematically in the figures. The same references in the individual figures in this case designate the same elements or elements with the same functions or elements that correspond with one another with regard to their functions.

The figures are as follows, in which, in detail.

EXEMPLARY EMBODIMENTS

Figure 1:
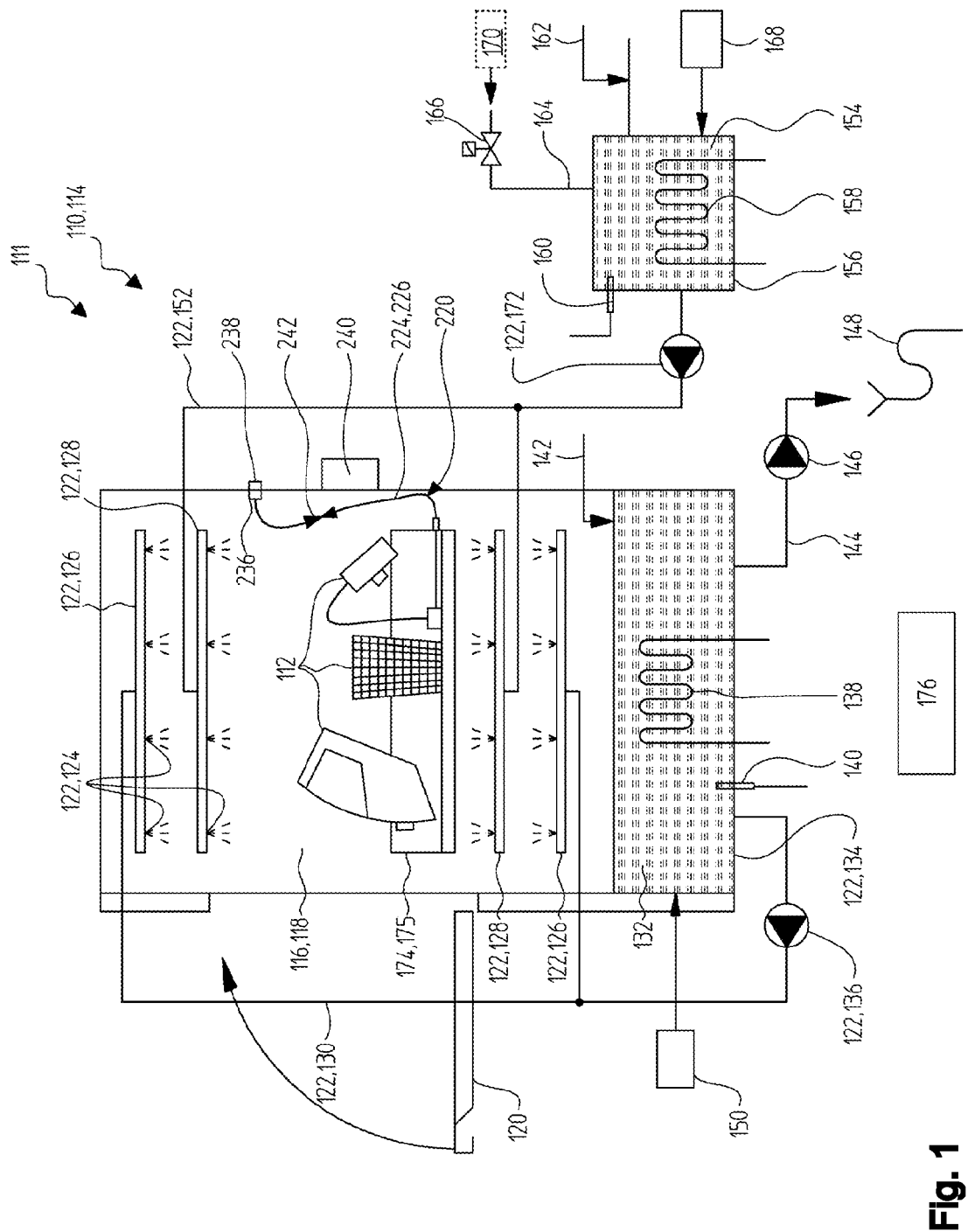
FIG. 1 shows a sectional representation of an exemplary embodiment of a cleaning apparatus for use in a cleaning system according to the invention.

FIG. 1 shows an exemplary embodiment of a cleaning apparatus 110 which is set up for cleaning one or several breathing apparatuses 112 and which is a component part of a cleaning system 111 according to the invention. The cleaning apparatus 110 is shown schematically in a sectional representation in FIG. 1. The cleaning apparatus 110 can be developed, for example, as a washer 114. The cleaning apparatus 110 includes a cleaning chamber 116, for example a wash chamber 118. Said cleaning chamber 116 can be opened, for example, by a door 120, for example a hinged door, a sliding door or a flap, and/or by another opening device. As an alternative to this or in addition to it, the cleaning chamber 116 can also be developed as a cleaning chamber that is covered by a cover. Other developments are also possible. In the exemplary embodiment shown in FIG. 1, the washer 114 is developed for example as a front loader washer. However, other developments are also possible.

The cleaning apparatus 110 comprises at least one fluid device 122 for applying one or several cleaning fluids onto the breathing apparatuses 112 which are received in the cleaning chamber 116. For example, the fluid device 122 can include one or several nozzles 124 which can be arranged, for example, above and/or below the breathing apparatuses 112 and/or at other locations inside the cleaning chamber 116, for example on one or several side walls. For example, the fluid device 122, as in the exemplary embodiment shown according to FIG. 1, can include a washing nozzle system 126, for example with one or several nozzle arms, which are accommodated below and/or above the breathing apparatuses 112, are preferably mounted so as to be rotatable and/or pivotable and have several nozzles 124. As an alternative to this or in addition to it, the fluid device 122 can also include a rinsing nozzle system 128, for example with one or several rinsing nozzle arms, which are preferably once again mounted so as to be rotatable and/or pivotable and once again can be accommodated, for example, above and/or below the breathing apparatuses 112. Other arrangements and/or developments, however, are also possible in principle.

The fluid device 122 can include over and above this one or several further elements such as, for example, one or several pipelines, one or several pumps and/or one or several tanks. Thus, for example, at least one wash line system 130 is provided in the exemplary embodiment shown, for applying cleaning fluid 132, for example detergent solution, from one or several wash tanks 134 onto the washing nozzle system 126. For example, a wash tank 134 can be provided in the bottom region of the cleaning chamber 116 and/or can be connected in another manner to the cleaning chamber 116 such that cleaning fluid 132 is able to flow and/or drip back again into the wash tank 134 after being applied onto the breathing apparatuses 112. For applying cleaning fluid 132 from the wash tank 134 to the washing nozzle system 126, the fluid device 122 can additionally comprise one or several recirculating pumps 136. In addition, one or several heating elements 138 can be provided to heat the cleaning fluid 132 of the wash tank 134 and/or other tanks, for example in the form of a wash tank heating means inside the wash tank 134. One or several temperature sensors 140 can be provided to control the heating of the cleaning fluid 132, for example inside the wash tank 134. In addition, one or several level sensors 142 can be provided, for example a level sensor 142 as level sensor of the wash tank 134. The wash tank 134 can be drainable into an outlet 148 for example by means of an outlet pipe 144 and as an option by means of a drain pump 146. As an option, one or several inlets to the wash tank 134, not shown in FIG. 1, can also be provided to fill said wash tank with cleaning fluid 132. As an alternative to this or in addition to it, filling can however also be effected by means of the rinsing nozzle system 128 which is described in more detail below. In addition, a dosing system 150 can be provided, for example at least one dosing system, to introduce one or several additives into the cleaning fluid 132 of the wash tank 134, for example a detergent concentrate, a rinsing agent, a disinfecting agent or combinations of the named and/or other additives.

The cleaning fluid 132 can be applied onto the breathing apparatuses 112 in particular in a recirculation mode by the cleaning fluid 132 being sprayed and/or injected out of the wash tank 134 by means of the washing nozzle system 126 onto the breathing apparatuses 112 in order to then to run back or drip back again into the wash tank 134 in order to be used once again from there. As an option, one or several filters, for example coarse filters and/or fine filters, can be provided in order to purify the cleaning fluid 132 of the wash tank 134 at least in part.

A further cleaning fluid 154, for example a rinse liquid, can be applied to the rinsing nozzle system 128, for example by means of at least one rinse line system 152. In this case, FIG. 1 shows an optional development where the cleaning apparatus 110 is developed as a two-circuit system. Accordingly, the second cleaning fluid 154 is provided from a separate tank which is developed in the exemplary embodiment shown as a rinse tank 156 which is realized separately from the wash tank 134. For example, said rinse tank 156 can be developed as a boiler and can include, for example, a rinse tank heating means 158. As an alternative to said rinse tank heating means 158 or in addition to it, other types of heating elements can also be provided for the second cleaning fluid 154, for example one or several instantaneous heaters. The same also applies to the first cleaning fluid 132 in the wash tank 134. Once again, one or several temperature sensors 160 and/or one or several level sensors 162 can be provided in the rinse tank 156, and the rinse tank 156 can be charged with cleaning fluid 154, for example fresh water, by means of one or several inlets 164. The at least one inlet 164 can comprise one or several valves 166. For example, the inlet 164 can be connected to or can be connectable to a fresh water connection on the building side. As an alternative to this or in addition to it, at least one reverse osmosis device 170 can be provided on the building side or as a component part of the cleaning apparatus 110, by means of which reverse osmosis device a permeate, for example purified water, is able to be applied to the rinse tank 156 and/or to one or several other tanks of the cleaning apparatus 110. In addition, once again at least one dosing system 168 can be provided, by means of which one or several additives can be added to the cleaning fluid 154 in the rinse tank 156, for example one or several rinse concentrates.

The rinse nozzle system 128 can preferably be acted upon in simple mode, that is not in recirculation mode, such that the rinse fluid from the rinse tank 154 is applied just once to the breathing apparatus 112. The fluid device 122 can include for example one or several pressure booster pumps 172 for the application.

The cleaning of the breathing apparatuses 112 in the cleaning apparatus 110 according to FIG. 1 can be effected, for example, as a result of one or several breathing apparatuses 112 initially being moved into the cleaning chamber 116 by means of a suitable holder 174, which is explained in more detail below and which is also a component part of the cleaning system 111. Along with the cleaning apparatus 110, the cleaning system 111 additionally includes a product range 175 of different holders 174 which are explained in more detail below and which can be moved into the cleaning chamber 116 in a selective manner. However, cleaning devices 110 where several holders 174 can be moved into the cleaning chamber 116 at the same time are also conceivable.

Once the holder 174 has been moved into the cleaning chamber 116, the door 120 can be closed, and a cleaning program which can be controlled by means of a control means 176, for example a central machine control means or a decentralized control means, can preferably be started. In this case, the wash tank 136 can first of all be filled for example by means of the rinsing nozzle system 128 with cleaning fluid 132 and/or a preliminary step of said cleaning fluid 132, for example fresh water, in particular demineralized fresh water. This can then be conditioned inside the wash tank 134, for example by adding one or several additives by means of the dosing system 150 and/or by heating by means of the heating element 138. As an alternative to this or in addition to it, the cleaning fluid 132 can also be left in the wash tank 134 after a rinse program of a preceding cleaning cycle in order to be utilized in a following cleaning cycle as cleaning fluid 132 and/or as a component part of the same, since rinse fluid, as a rule, comprises a comparatively high degree of purity even after being applied to the breathing apparatus 112.

The breathing apparatus 112 can then be cleaned, in particular washed, preferably in recirculation mode, in one or several wash program steps. In this connection, adhering contaminants can be removed from the breathing apparatuses 112, and/or the breathing apparatuses 112 can be sterilized.

One or several rinse steps can preferably be carried out following the at least one wash program step. To this end, the wash tank 134 can be drained as an option by means of the outlet line 144 and the drain pump 146. The rinse tank 156 can already have been filled with rinse fluid 154, for example fresh water with or without additives, for example demineralized fresh water, during the at least one wash program step. One or several additives can then be added by means of the dosing system 168 and/or the cleaning fluid 154 as rinse fluid can be heated by means of the rinse tank heating means 158 and/or an instantaneous heater. The rinse fluid 154, preconditioned in this manner, can then be applied to the breathing apparatuses 112 in the at least one rinse step by means of the rinsing nozzle system 128 such that they are rinsed and/or finally rinsed. After the at least one rinse step, as an option once again at least one drying step can follow which can be developed in a passive manner, as a result of simply waiting, or which can also be actively supported, for example by means of at least one drying fan and/or another type of drying device of the cleaning apparatus 110, for example an infrared radiation system and/or a microwave system. Different developments are conceivable. Following the optional drying step, the door 120, which has preferably been locked up to then as an option, can be automatically released and/or opened. The entire program sequence can be controlled for example by the control means 176, it also being possible to choose several program sequences.

It is pointed out that the exemplary embodiment of the cleaning apparatus 110 shown in FIG. 1 simply provides one exemplary embodiment of several different ones. Thus, individual or several or all of the above-described elements can also be realized within another framework. The wash chamber 118, as an alternative to the rigid, stationary development according to FIG. 1 or in addition to it, can also be developed so as to be pivotable and/or rotatable. In addition, the fluid circuit shown can also be considerably modified.

As shown above, the at least one breathing apparatus 112 is held inside the cleaning apparatus 110 preferably by means of at least one holder 174. In this case, different holders 174 of this type are provided within the framework of the cleaning system 111. FIG. 1 simply shows a schematic representation of one possible exemplary embodiment of a holder 174 of this type.

Exemplary embodiments of possible holders 174 of a possible product range 175 of holders 174 are shown in FIGS. 2 to 13. Common to the following exemplary embodiments is that they comprise a basic basket 178, which is shown as an example in FIG. 2, and different sets. The basic basket 178 can be connected for example in a reversible manner to the sets and can be used in all the holders 174.

Figure 2:
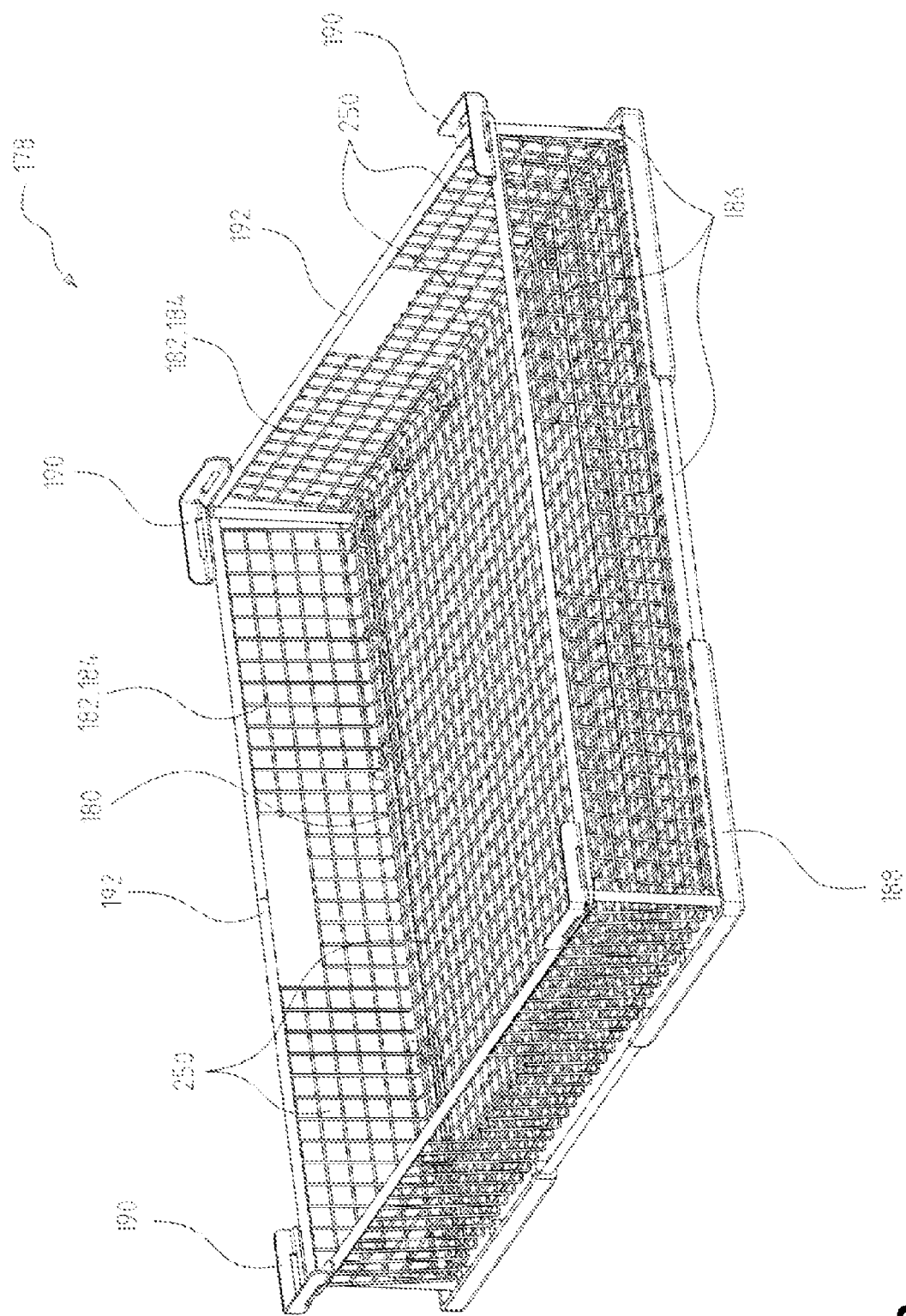
FIG. 2 shows an exemplary embodiment of a basic basket for use in a product range according to the invention.

The basic basket 178 shown as an example in FIG. 2 comprises a bottom part 180 and side walls 182 in the form of a raised edge 184. The bottom part 180 can be developed, for example, as a flat bottom part, for example with a rectangular area, and can comprise, for example a frame 186 with edge protection 188. Positioning aids 190, into which the sets described in more detail below can be inserted, are provided on the upper, circumferential edge of the side walls 182. The basic basket 178 can comprise, for example, carrying handles 192. The basic basket can be produced, for example, from wire mesh, for example with an aperture of 10 mm. However, other developments are also possible in principle. Reference can be made in this regard, for example, to the above description.

Figure 3:
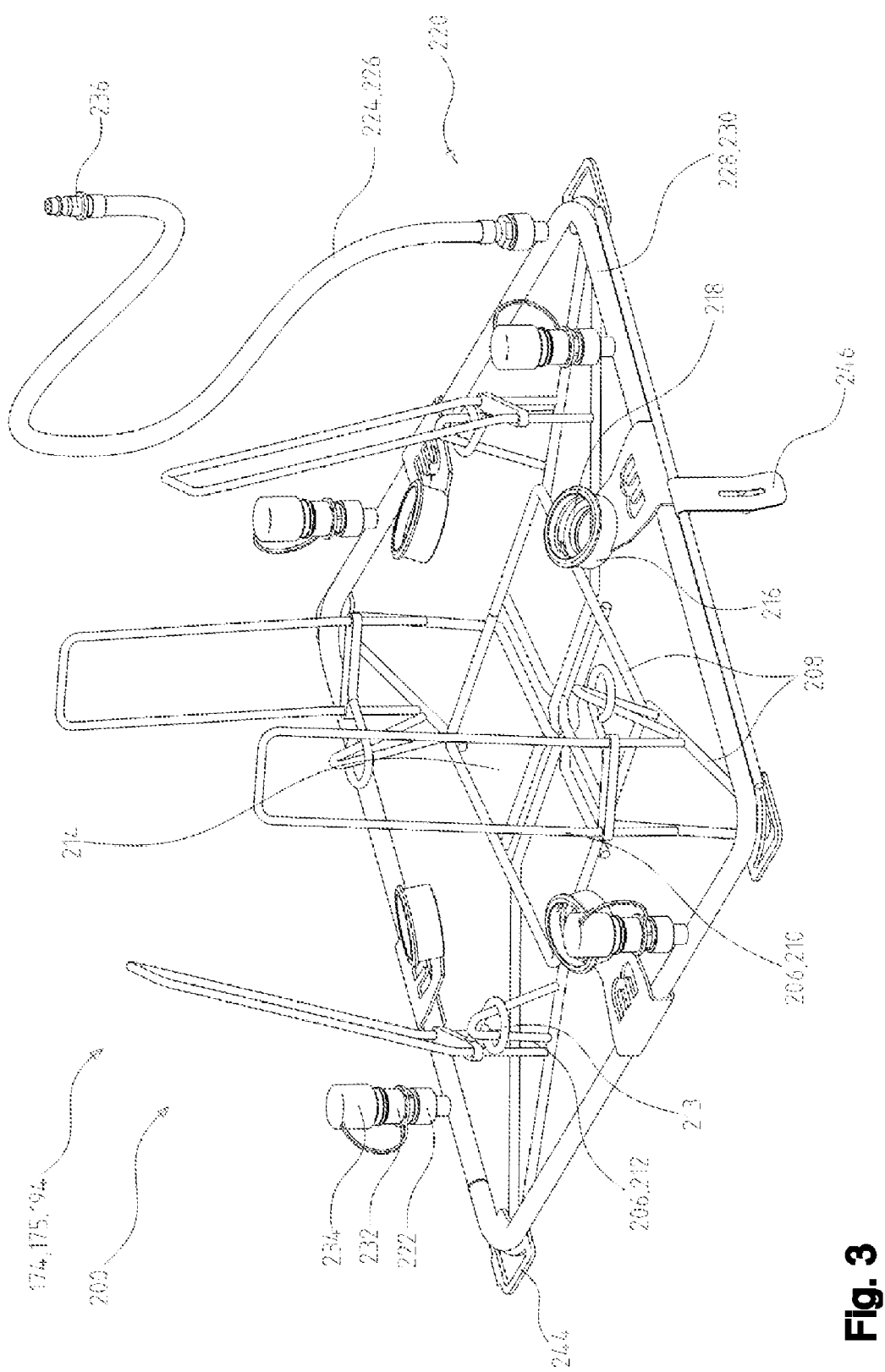
FIG. 3 shows an exemplary embodiment of a first set for use in a first holder.
Figure 4:
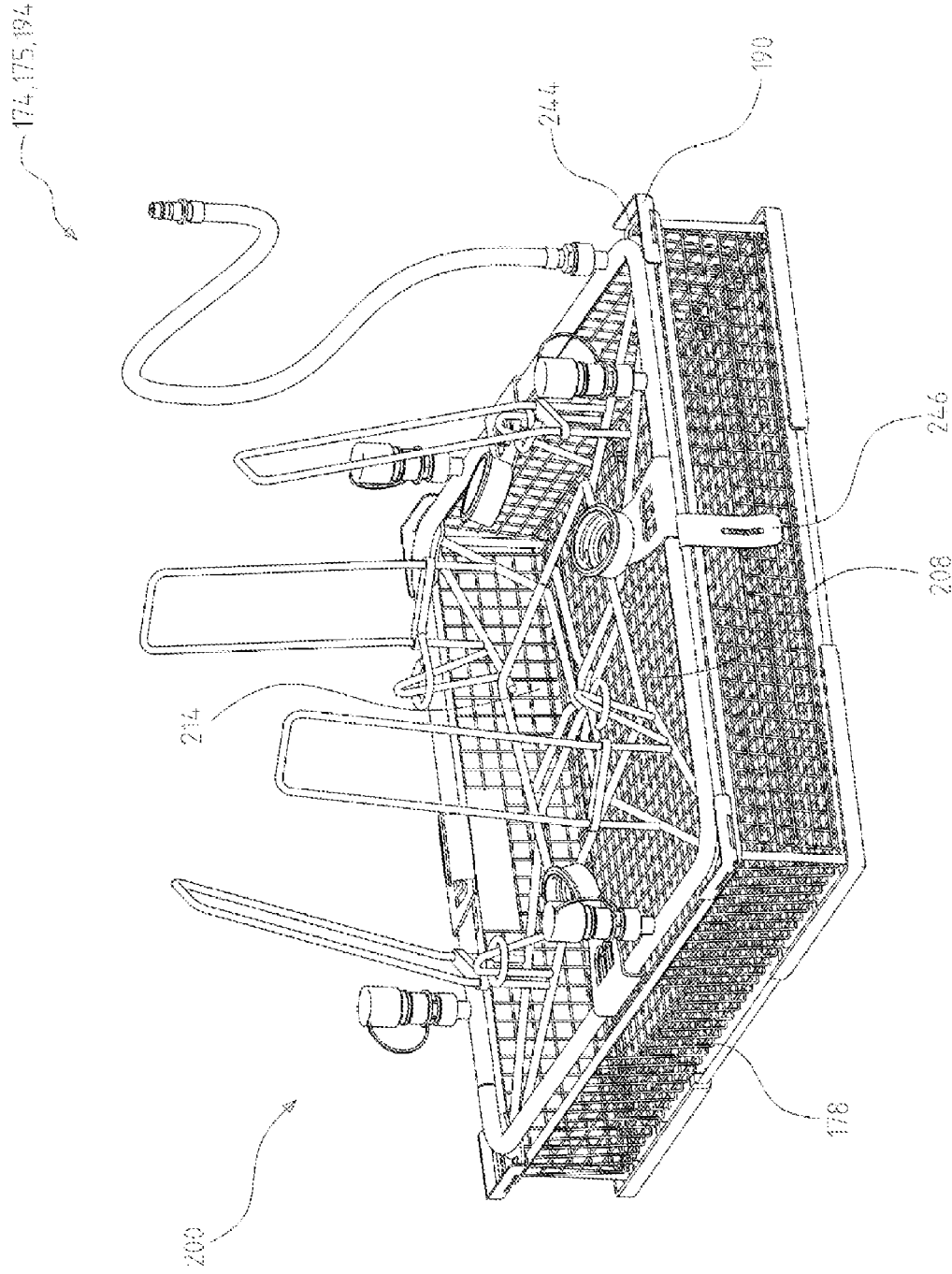
FIG. 4 shows an exemplary embodiment of a first holder.
Figure 5:
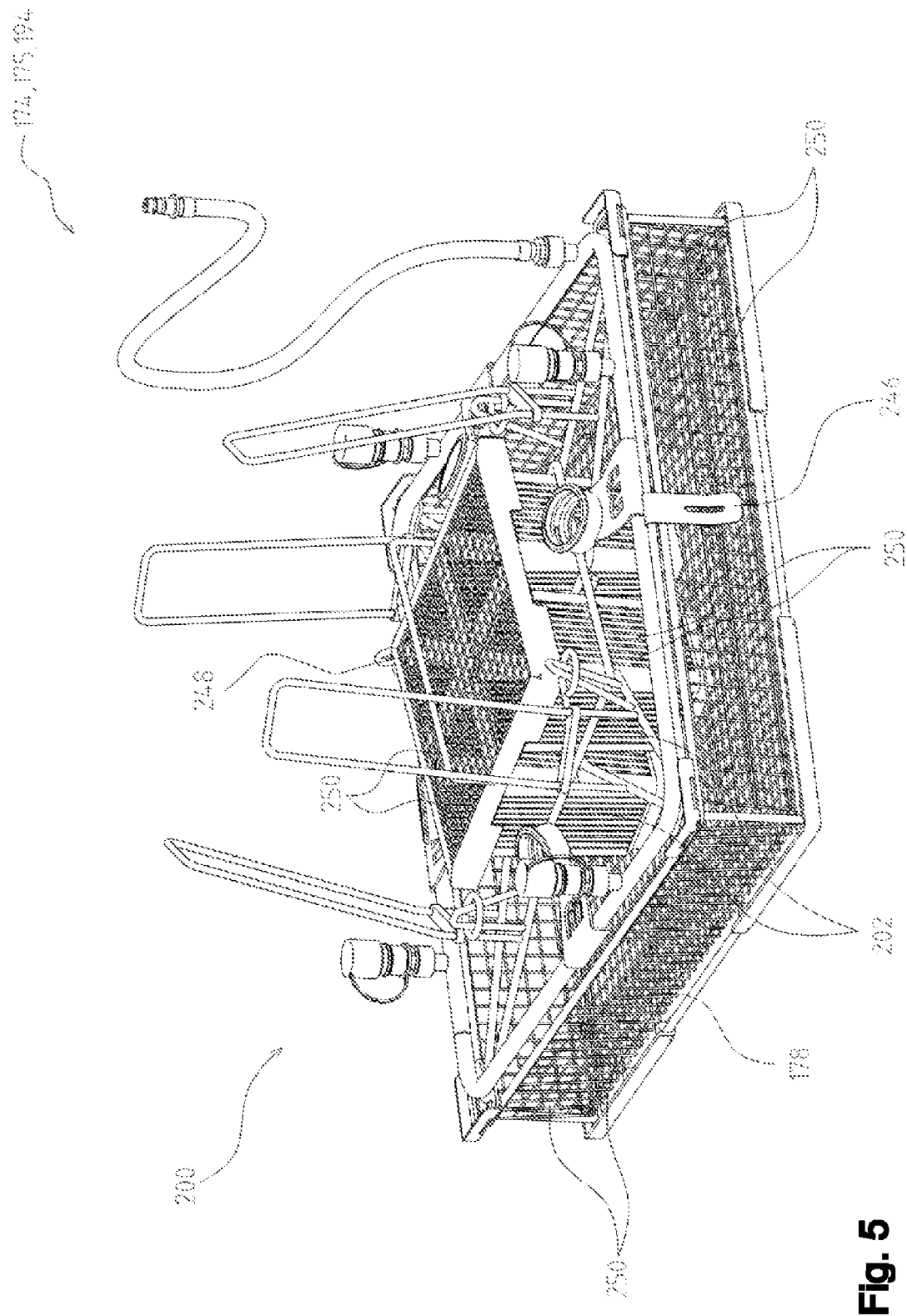
FIG. 5 shows the exemplary embodiment according to FIG. 4 additionally with a plurality of small parts baskets.
Figure 6:
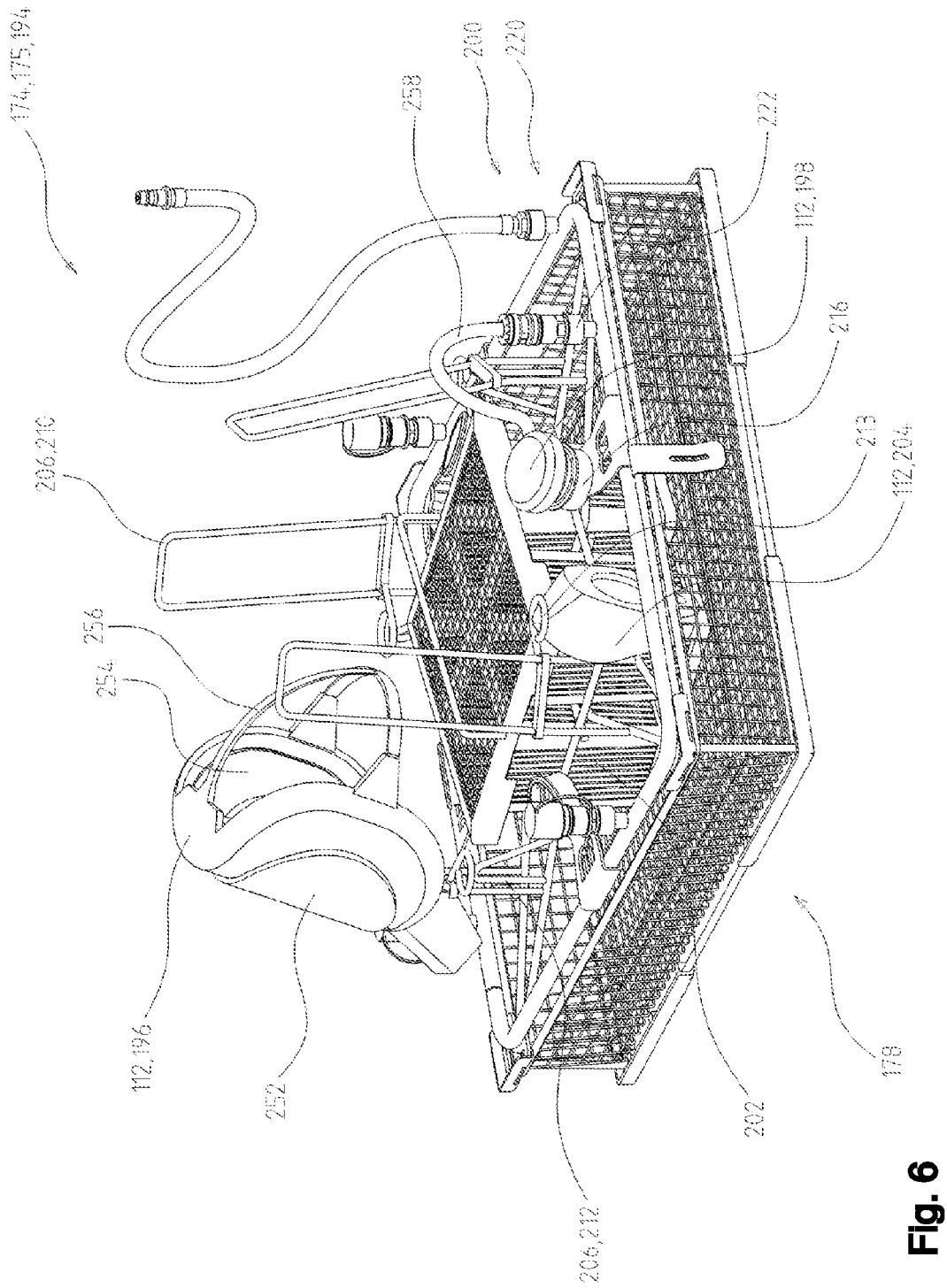
FIG. 6 shows the exemplary embodiment according to FIG. 5, fitted out as an example with a breathing mask, an inner mask and a breathing valve.

As stated above, the product range 175 comprises at least two holders 174. FIGS. 3 to 6 show, in different representations, an exemplary embodiment of a possible first holder 194 of the product range 175. Said figures are explained below in a substantially common manner. The first holder 194 serves for cleaning breathing masks 196 and breathing valves 198 at the same time. In this case, FIG. 3 shows an exemplary embodiment of a first set 200 which can be fitted onto the basic basket 178 according to FIG. 2, FIG. 4 shows the first holder 194 after fitting the first set 200 onto the basic basket 178, FIG. 5 shows the exemplary embodiment according to FIG. 4 supplemented by a plurality of small parts baskets 202, and FIG. 6 shows the exemplary embodiment according to FIG. 5, a breathing mask 196, an inner mask 204 and a breathing valve 198 being received as an example in the first holder 194.

The first holder 194 and there in particular the first set 200, as shown in FIG. 3, comprises locations for in each case four breathing masks 196, four inner masks 204 and four breathing valves 198. However, another number of locations can also be provided.

Thus, the first set 200 comprises mask holding devices 206. These are realized in the form of a framework 208 which comprises holding brackets 210 for the breathing masks 196 as well as holding brackets 212 for inner masks 204.

As an option, the mask holding devices 206 can also be developed in another manner in this or also in other exemplary embodiments of the invention or can comprise, for example in addition to the holding brackets 212 for the inner masks 204, also one or several further elements. Thus, for example, as shown in FIG. 3, each holding bracket 212 or a group of several holding brackets 212 has assigned thereto in each case at least one hold-down device 213.

Said hold-down device 213 can be or comprise, for example, a movable element which can comprise, for example, an open position and a closed position. In the open position, for example, at least one inner mask 204 can be moved onto at least one holding bracket 212, and/or at least one inner mask 204 can be removed from the at least one holding bracket 212. In the closed position, for example, it can be ensured that the inner mask 204 is fixed during a cleaning operation such that it is not able to slip for example off its respective holding bracket 212. FIG. 3 shows a closed position of the hold-down device 213. In order to move the hold-down device 213 into an open position, it can be displaced, for example, upward. The transferring of the at least one optional fixing element, for example the hold-down device 213, from the closed into the open position or vice versa can be effected, for example, manually and/or also automatically. This latter, for example, as a result of at least one optional actuator of the cleaning apparatus 110 which has been set up correspondingly.

The hold-down device 213 can be connected, for example, entirely or in part to one or several of the holding brackets 210 and/or 212, preferably in a movable manner. Thus, for example, in each case one hold-down device 213 can be mounted so as to be displaceable on in each case one holding bracket 212 or holding bracket 210 (latter option is shown in FIG. 3). In this way, the hold-down device 213 can be transferred, for example, from a closed position into an open position or vice versa as a result of simple displacement.

The hold-down device 213 is simply an example for possible fixing elements for fixing the at least one breathing mask 196 and/or the at least one optional inner mask 204. As an alternative to a hold-down device 213 or in addition to it, one or several other types of fixing elements can be provided in this or also in other exemplary embodiments for fixing the breathing masks 196 and/or the inner masks 204.

In addition, the framework 208 can comprise a plurality of receiving means 214 for the small parts baskets 202.

In addition, the first set 200 in said exemplary embodiment comprises a plurality of breathing valve holding devices 216. In said exemplary embodiment, four of these types of breathing valve holding devices 216 are provided as an example. These can comprise, for example, in each case a round receiving means, into which a connecting piece of the breathing valve can be plugged. Inside said receiving means of the breathing valve holding device 216, in each case friction brakes 218 can be provided, for example for holding the breathing valves 198 in a friction locking manner. Said friction brakes 218 can be realized, for example, by sealing rings produced from an elastomer material.

In addition, the first holder 194 and the first set 200 comprise a pressurizing device 220 with, in this case, a plurality of pressure connections 222. In the exemplary embodiment shown, the pressurizing device 220 comprises a compressed air supply 224 in the form of a hose 226 which opens out in a pressurized gas line 228. Said pressurized gas line 228 in said exemplary embodiment is developed as a carrying component and forms a frame 230. Said frame 230, which is developed in a ring-shaped manner and comprises a rectangular cross section, sits on the framework 208 in said exemplary embodiment, and the breathing valve holding devices 216 are pushed onto said frame 230 and are preferably welded on. As an alternative to welding on or in addition to it, other types of connection can also be provided, for example positive locking and/or non-positive locking connections and/or bonding. In addition, the pressure connections 222 are fitted onto said frame 230 such that a continuous fluid connection is preferably formed from the coupling 236 via the hose 226 and the pressurized gas line 228 up to the coupling 232 on the pressure connection 222.

The pressure connections 222 include on their upper end in each case a coupling 232, to which in each case a pressurized gas hose of a breathing valve 198 can be connected. Said coupling 232 is closable by a removable cap 234 when no breathing valve is connected.

The hose 226 also comprises a coupling 236 at its free end. By way of said coupling 236, as shown schematically in FIG. 1, the hose 226 is able to be connected to an apparatus-side pressurizing device 238 of the cleaning apparatus 110. In this connection, this can be, for example, a pressurized gas connection, for example a compressed air connection, which can be connected or is connected to a building-side pressure supply and/or the cleaning apparatus 110 can include an integrated pressurized gas source 240, for example a compressed air cylinder and/or a compressor. In addition, one or several valves 242 can be provided in the hose 226 and/or between the pressurizing devices 220, 238.

The first set 200 shown in FIG. 3 comprises in each case widened supporting corners 244 at its corners. The first set 200 is fitted onto the basic basket 178 and there in particular onto the positioning aids 190 by means of said supporting corners, which can be component parts of the framework 208 for example and/or can be connected to said framework 208, and on which, for example, the frame 230 can also rest on the framework 208. This can be seen, for example, in the assembled state according to FIG. 4. In this case, the first set 200 is preferably simply fitted onto the basic basket 178. In addition, in this case, one or several connecting elements 246 can be provided which secure the connection between the basic basket 178 and the first set 200. In the exemplary embodiment shown, a connecting element 246 in the form of a latching hook is provided, for example, on the framework 208 such that, for example, a latching connection is producible between the basic basket 178 and the first set 200. However, other developments are also possible.

The first set 200 or, selectively, other sets, can be connected, for example, to the basic basket 178 in such a manner that the respective set is initially fitted onto the basic basket 178. The supporting corners 244 can comprise, for example, in each case one or several continuations and/or tongues which can engage in suitable slots and/or openings on the positioning aids 190. On said side of the respective holder, a positive locking connection can be produced, for example, between the respective set and the basic basket 178. The connecting element 246 can be developed, for example, as a latching hook or can comprise at least one latching hook which can engage in the edge 184 on the basic basket 178 for producing a connection for example at the top. For example, at least one latching connection can be produced in this way or in a different way. For releasing the connection, in particular for separating the respective set from the basic basket 178, for example the connecting element 246 can be moved and/or deformed. For example, said connecting element 246 can be turned and/or pivoted manually outward in order to release the connection. As an alternative to this or in addition to it, however, other developments are also conceivable.

In the state shown in FIG. 4, the first holder 194 is basically ready for use. However, in many cases, as already mentioned above, it is expedient additionally to provide small parts baskets 202 which can be fitted into the receiving means 214 in the framework 208. FIG. 5 accordingly shows the first holder 194 according to FIG. 4 with small parts baskets 202 additionally inserted into the receiving means 214. Said small parts baskets 202 can be closable, for example, by a common cover 248 in order to prevent the small parts falling out. The receiving means 214, in this case, are positioned in such a manner in the framework 208 that in each case they are assigned a mask holding device 206 and a breathing valve 216. In this case each pair, consisting of a breathing mask 196 and a breathing valve 198, has assigned thereto in each case a small parts basket 202 such that protection against a mix-up is ensured.

Both the basic basket 178 and the small parts baskets 202, along with the cover 248 as an option, comprise in each case a plurality of openings 250, as shown as an example in FIG. 5. Said openings 250 can be, for example, mesh openings in a wire mesh of the basic basket, preferably both in the bottom part 180 and in the side walls 182. In the case of the small parts baskets 202, the openings 250 can be, for example, slot-shaped openings in the side walls and/or openings in a bottom part (not shown in any more detail) of the small parts baskets 202. In the cover part 248, the openings 250 can be developed, for example, in the form of mesh openings. With reference to the basic basket 178, for example mesh apertures of approximately 10 mm are preferred. The openings 250 on the one hand enable the spray jets of the cleaning fluid 132 to penetrate uniformly and on the other hand to drain away after being applied onto the breathing apparatus 112.

FIG. 6 finally shows the first holder 194 in a state in which a breathing mask 196 has been put over a holding bracket 210 of a mask holding device 206 as an example, in such a manner that a viewing window 252 of the same points outward at an angle and that an inside surface 254 points upward. Holding straps 256 of the breathing mask 196 can project loosely into the interior of the first holder 194 in this case.

In addition, as stated above, an inside mask 204 is fitted onto a holding bracket 212 as an example. In addition, as an option, once again at least one hold-down device 213 and/or another type of fixing element can be provided for the at least one inner mask 204 and/or also for the breathing mask 196. This is once again shown as an example in FIG. 6. For example, once again, as stated above, in each case at least one hold-down device 213 for in each case an inner mask 204 can abut against the inner mask 204 from above in a closed state (as shown) in order to prevent the inner mask 204 from slipping during a cleaning operation. For placing and/or removing the inner mask 204, the hold-down device 213 can be moved, for example, into an open position, for example by said hold-down device being displaced upward. In addition, a breathing valve 198 is inserted into a breathing valve holding device 216, and an air hose 258, also designated as a pressurized gas hose of the breathing valve 198 is coupled to a pressure connection 222 as an example.

Figure 7:
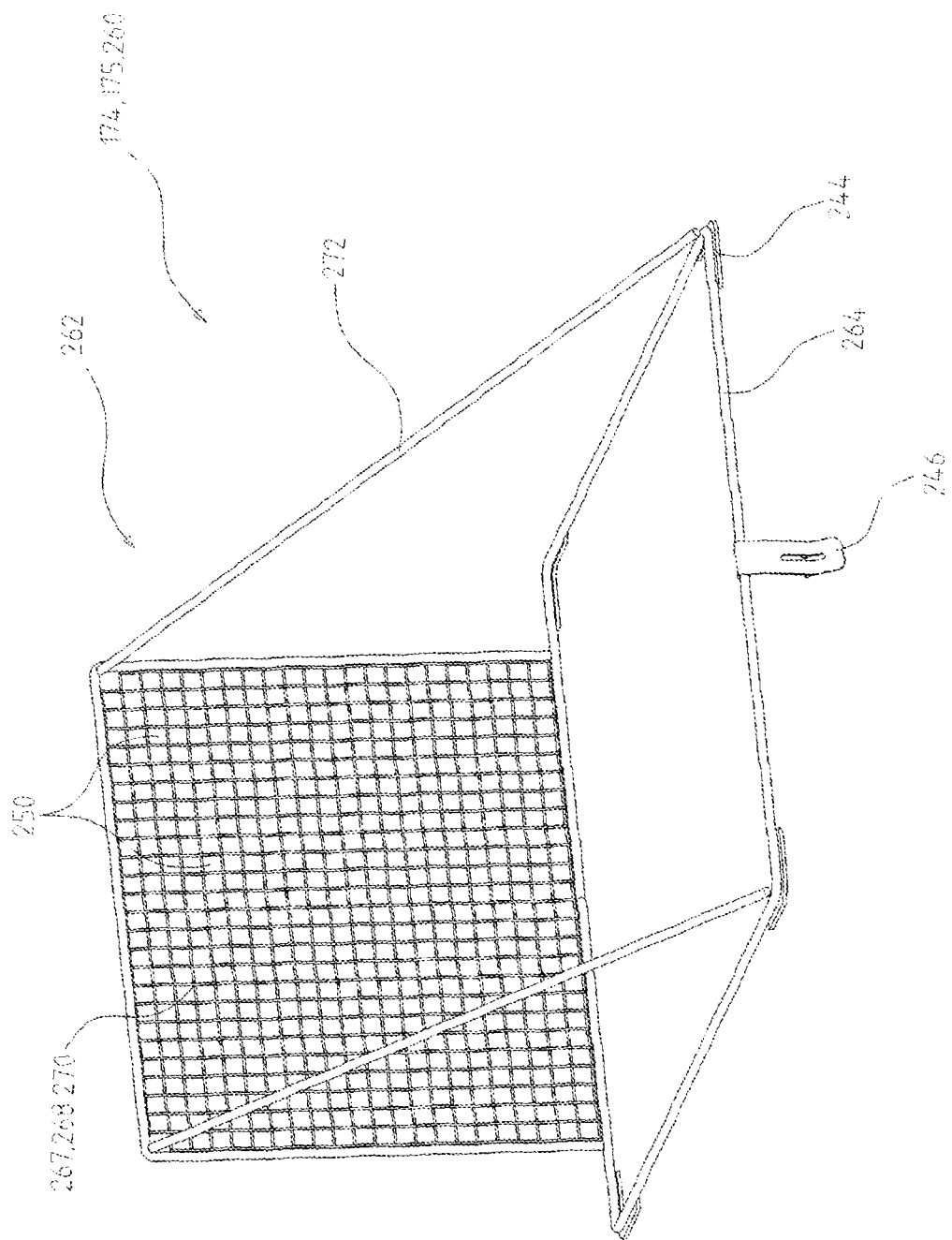
FIG. 7 shows an exemplary embodiment of a second set for use in a second holder.
Figure 8:
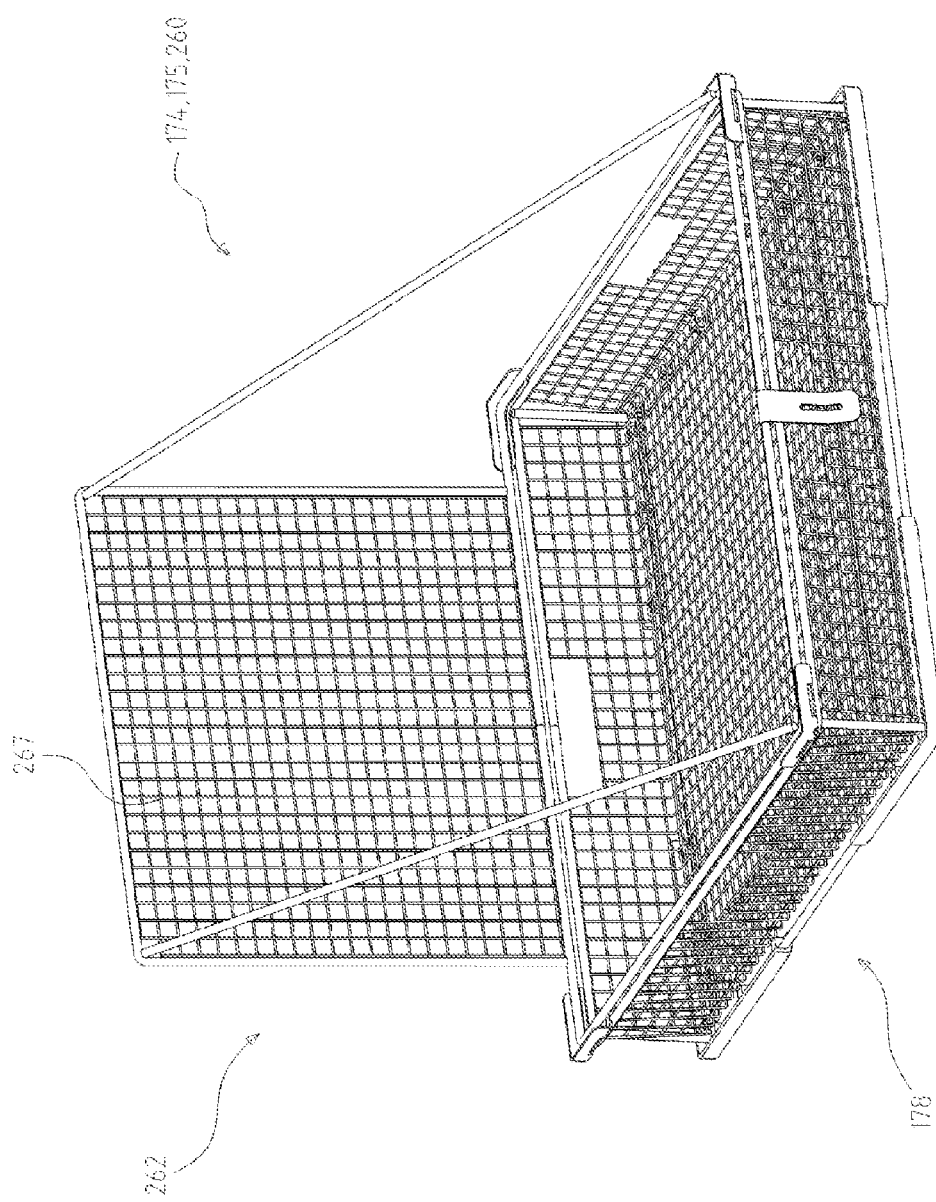
FIG. 8 shows an exemplary embodiment of the second holder.
Figure 9:
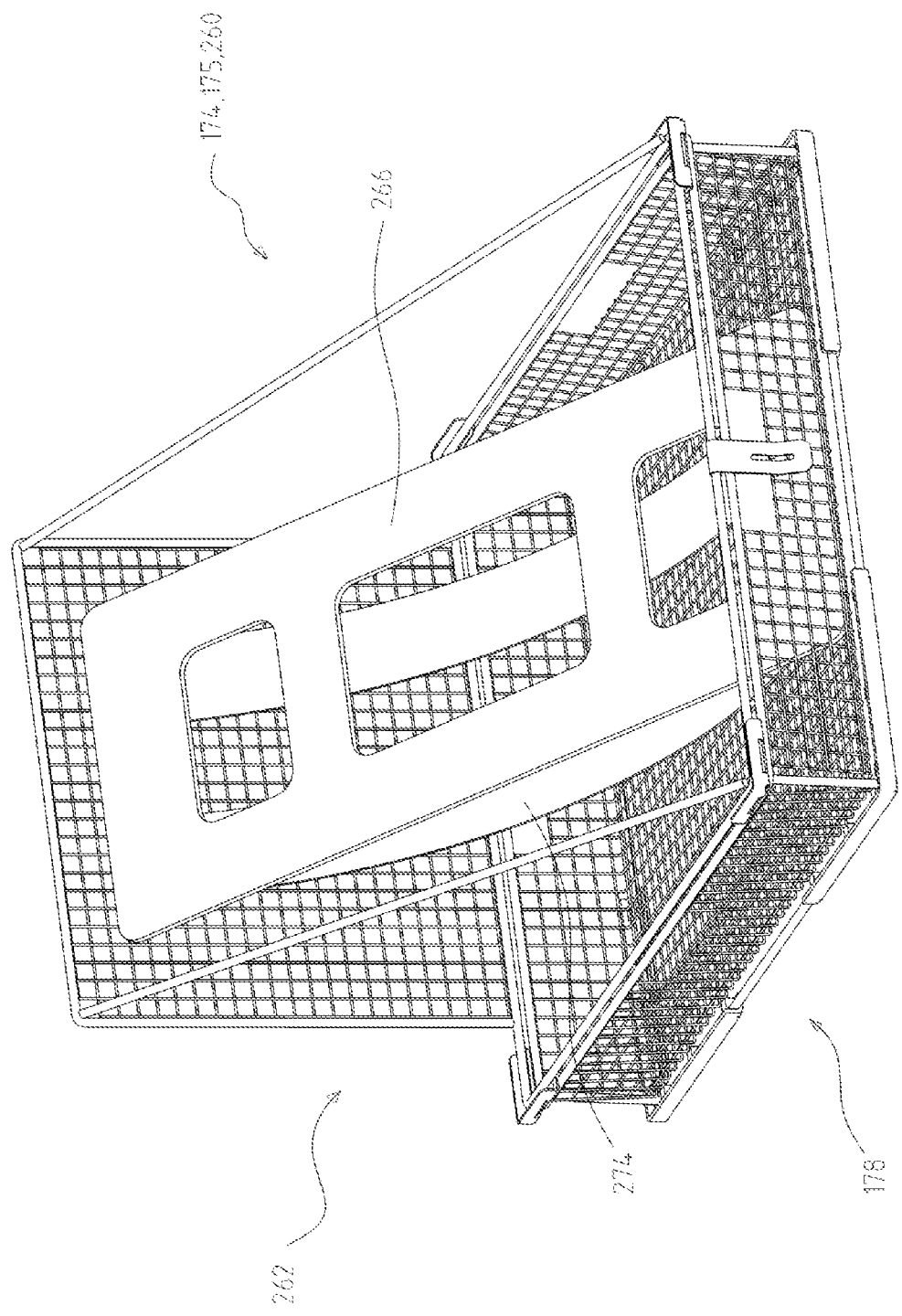
FIG. 9 shows the second holder according to FIG. 8 fitted out as an example with a carrying frame inserted.

FIGS. 7 to 9 show an exemplary embodiment of a second holder 260 of the product range 175 as an example. In this case, FIG. 7 once again shows a second set 262, which can be fitted into a basic basket 178 according to FIG. 2. For this purpose the second set 262 comprises a frame 264 which is rectangular and corresponds substantially to the area of the basic basket 178. Once again supporting corners 244 which can be fitted into the positioning aids 190 of the basic basket 178 can be provided on the corners of said frame 264. In addition, once again at least one connecting element 246 can be provided for connecting to the basic basket. With reference to possible developments of said connecting element 246, reference can be made, for example, to the above description of FIG. 4.

The second holder 260 serves for holding carrying frameworks 266 for pressurized gas cylinders. Said carrying frameworks 266 are shown as an example in FIG. 9. In order to support said carrying frameworks 266, the second set 262 comprises a perpendicular support 268 in the form, for example, of a flat plate 270 which is connected to the frame 264 and which is connected to the frame 264 and stabilized by means of transverse struts 272. In this case, the support 268 forms an exemplary embodiment of a carrying framework holding device 267. The flat plate 270 is developed for example as a wire mesh and comprises a plurality of openings 250, for example once again openings with a mesh aperture of 10 mm. In this way, cleaning fluid 132 is once again able to be applied onto the carrying framework 266 from all sides in an optimum manner.

FIG. 8 shows the second holder 260 in an assembled state in which the second set 262 is fitted onto the basic basket 178. FIG. 9, as mentioned above, finally shows a state where a carrying framework 266 is moved into the second holder 260. In this case, it can be moved in such a manner that the carrying framework 266 is received in the second holder at an angle to the horizontal, it being possible for carrying belts 274 to be received hanging loosely downward, toward the basic basket 178.

Figure 10:
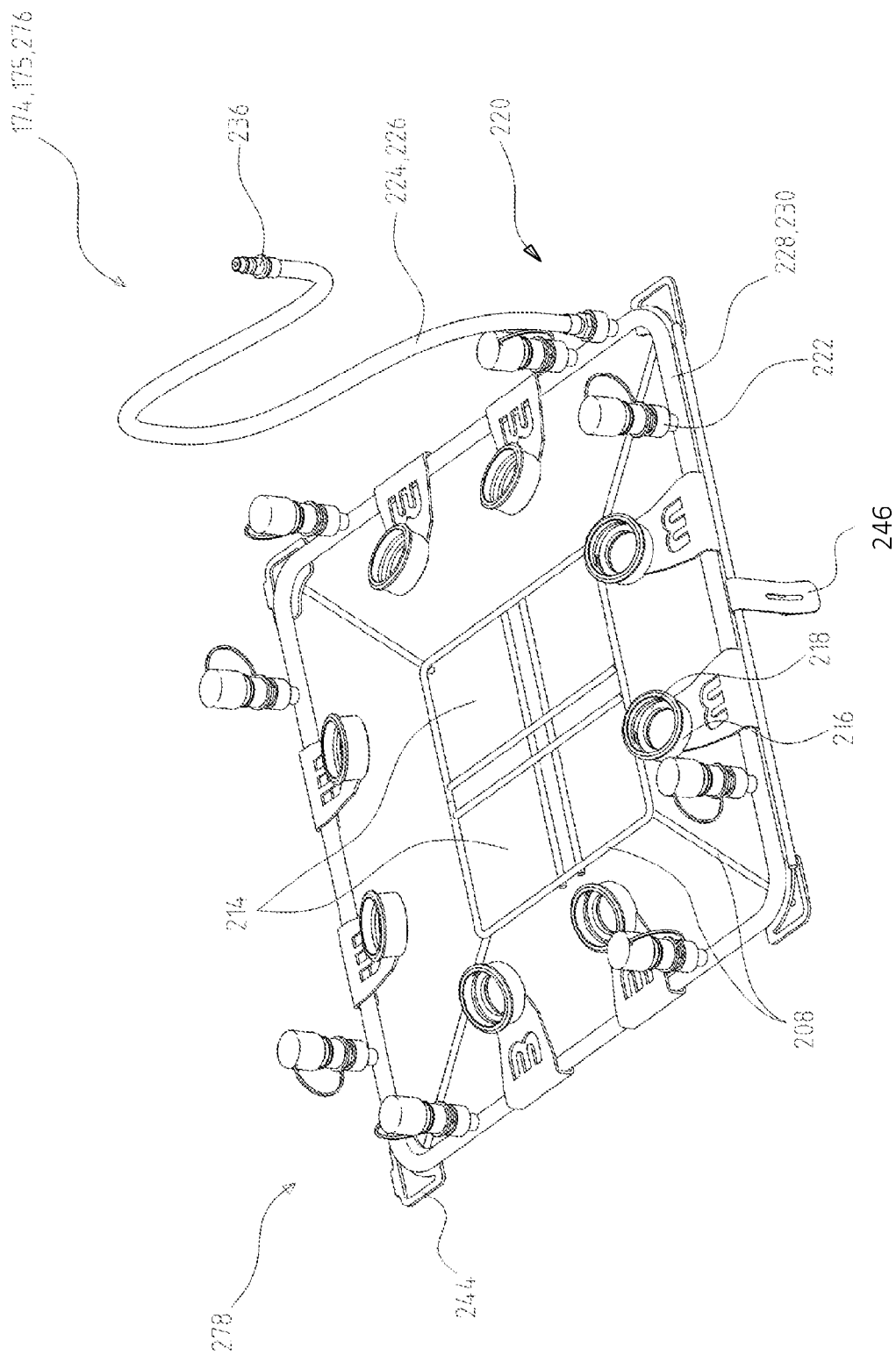
FIG. 10 shows an exemplary embodiment of a third set for use in a third holder.
Figure 11:
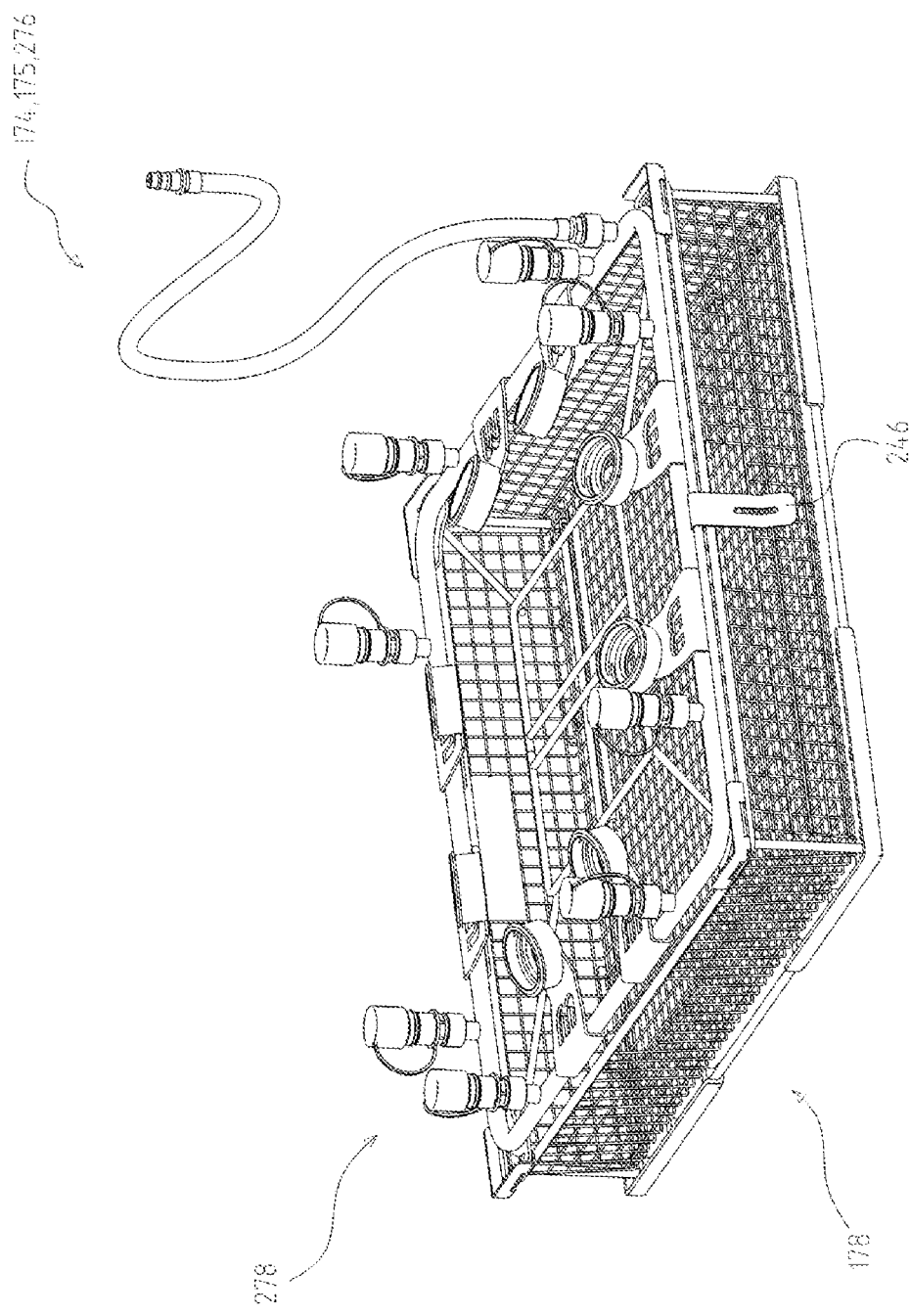
FIG. 11 shows an exemplary embodiment of a third holder.

FIGS. 10 and 11 show an exemplary embodiment of an optional third holder 276 of the product range 175. In this case, FIG. 10 shows a third set 278 which can be fitted onto a basic basket 178, for example according to FIG. 2. FIG. 11 shows an assembled state.

The third set 278 initially corresponds substantially to the first set 200, for example according to FIG. 3. However, said third set 278 does not comprise any mask holding devices 206. Accordingly, the third holder 276 and the third set 278 serve for cleaning breathing valves 198, not, in contrast, for cleaning breathing masks 196. For the description of the third set 278, reference can be made extensively to the above description. Thus, the third set 278 once again comprises a plurality of breathing valve holding devices 216, a pressure connection 222 of a pressurizing device 220 being provided for each breathing valve holding device 216, to which, analogously for example to the representation according to FIG. 6, an air hose 258 of a breathing valve 198 can be connected. The pressurizing device 220 once again comprises, analogously to FIG. 3, a compressed air supply 224 in the form of a hose 226, with a coupling 236 for connection to an apparatus-side pressurizing device 238 according to FIG. 1, as well as a pressurized gas line 228 in the form of a frame 230, onto which the pressure connections 222 are fitted. The frame 230 is once again developed in a ring-shaped manner and comprises a rectangular shape. In said exemplary embodiment, two breathing valve holding devices 216 and two pressure connections 222 are provided as an example on each side of the frame 230 such that a total of eight breathing valves 198 are able to be cleaned at the same time. Other developments are, however, also possible. The frame 230 can once again be developed as a carrying component and can carry the breathing valve holding devices 216. The frame 230 can once again rest, for example, on a framework 208 which comprises at its corners supporting corners 244 which can be fitted in the positioning aids 190 of the basic basket 178. In addition, the framework 208 can once again, as an option, comprise one or several receiving means 214 for one or several small parts baskets 202, which are not shown in FIGS. 10 and 11. With reference to the possible development of said small parts baskets 202, reference can be made to FIGS. 5 and 6 as an example. These same small parts baskets 303 can be used for the first holder 194 and the third holder 276 as they are preferably received loosely in the receiving means 214.

FIG. 11 shows the third holder 276 in a ready-to-use state, but without any small parts baskets 202. The third set 278, in this case, is fitted onto the basic basket 178, the supporting corners being fitted 244 in the positioning aids 190. As an option, once again at least one connecting element 246 can be provided, for example once again for producing a latching connection. With reference to possible developments of said connecting element 246, reference can be made to the above description of FIG. 4.

Figure 12:
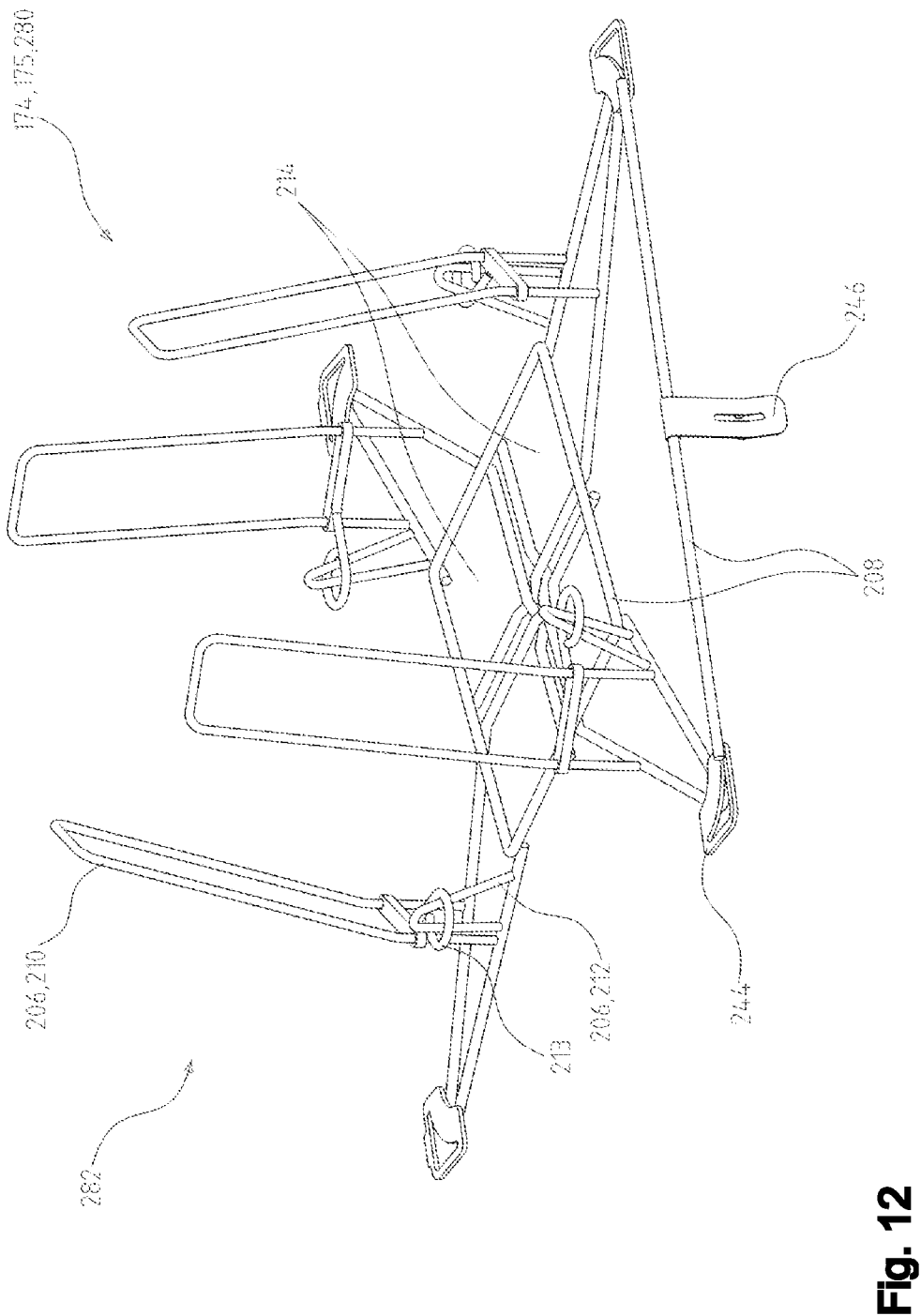
FIG. 12 shows an exemplary embodiment of a fourth set for use in a fourth holder.
Figure 13:
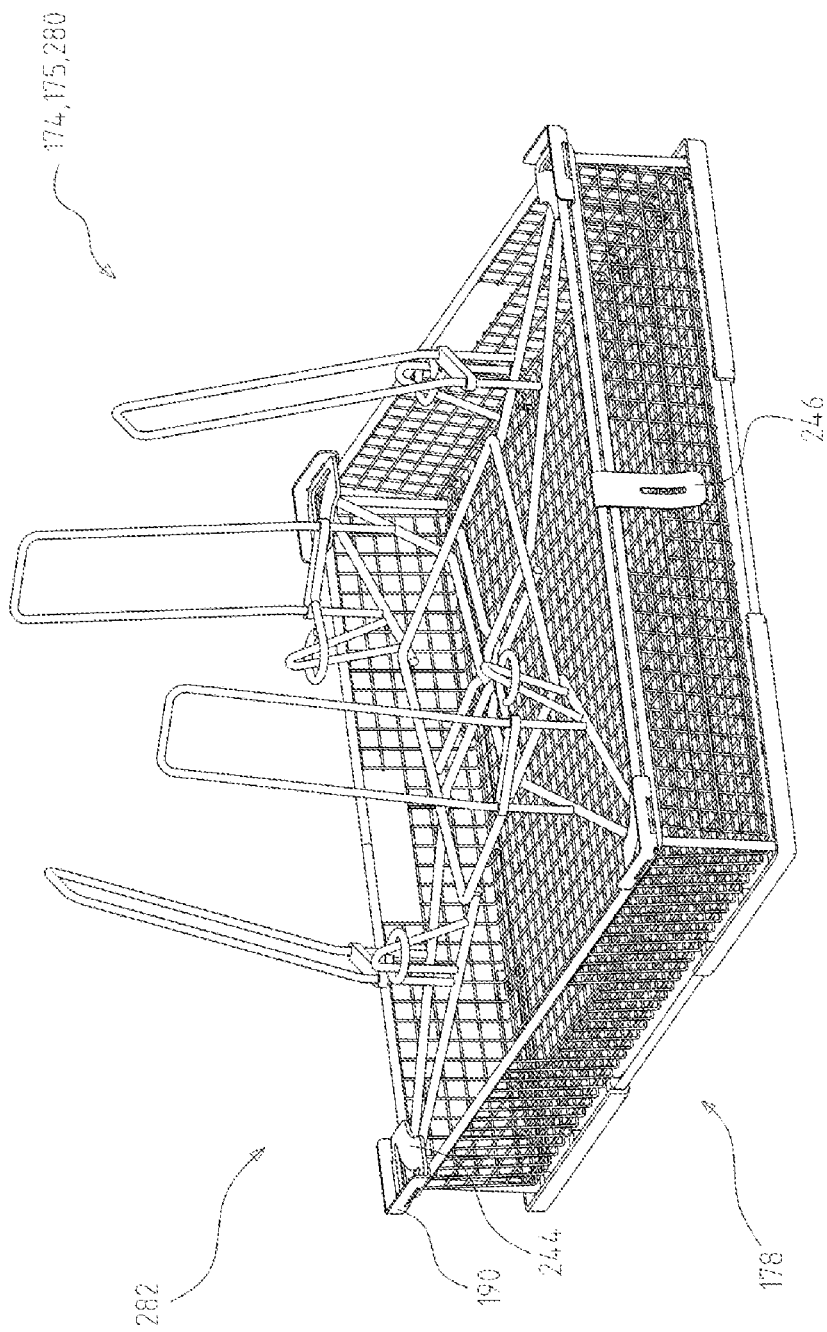
FIG. 13 shows an exemplary embodiment of a fourth holder.

FIGS. 12 and 13 show an exemplary embodiment of an optional fourth holder 280 of the product range 175 as an example. Said fourth holder 280 comprises a fourth set 282 which is shown in detail in FIG. 12 and which once again can be fitted into a basic basket 178, as shown in FIG. 13. Said fourth holder serves for cleaning breathing masks 196 such that reference can be made extensively in this connection to the description in FIGS. 3 to 6 above. Accordingly, the fourth set 282 of the fourth holder 280 once again includes at least one mask holding device 206. In the case of the fourth holder 280, however, no breathing valve holding devices 216 are provided.

The fourth set 282 once again comprises, analogously to FIGS. 3 to 6 above, a framework 208, for example a wire mesh. Holding brackets 210 for breathing masks 196 are provided on said framework 208, as well as, as an option, holding brackets 212 for inner masks 204. As stated above, the fourth set 282 can once again, as an option, comprise one or several fixing elements for fixing the breathing masks 196 and/or the inner masks 204. Thus, one or several hold-down devices 213 can once again be provided, for example, for the inner masks 204. In this regard, reference can be made to the above description as an example. Reference can also be made to the above description for further possible developments. Mask holding devices 206 for four breathing masks 206 as well as in a corresponding manner four inner masks 204 are provided as an example in said exemplary embodiment according to FIGS. 12 and 13. Reference can be made to the representation according to figure as an example for the possible fitting of the breathing masks 196 or the inner masks 204 onto said mask holding devices 206.

As an option, one or several receiving means 214 for receiving one or several small parts baskets 202, which are not shown in FIGS. 12 and 13, are provided once again as an option in the framework 208. Said small parts baskets 202 can be put into the receiving means 214 once again so as to be removable. Reference can be made to the above description as an example for the development of the small parts baskets 202. These same small parts baskets 202 can also be used in the fourth holder 280 which are also used, for example, in the first holder 194.

The framework 208 can once again comprise supporting corners 244 which can be inserted into the positioning aids 190 of the basic basket 178. This can be seen in the assembled state of the fourth holder 280 shown in FIG. 13. As an option, a connection can be effected once again additionally by one or several connecting elements 246, for example a latching connection. Reference can be made to the above description of FIG. 4 in this connection.

LIST OF REFERENCES

110 Cleaning device
111 Cleaning system
112 Breathing apparatuses
114 Wash machine
116 Cleaning chamber
118 Wash chamber
120 Door
122 Fluid device
124 Nozzles
126 Washing nozzle system
128 Rinsing nozzle system
130 Wash pipe system
132 Cleaning fluid, wash fluid
134 Wash tank
136 Recirculation pump
138 Heating element
140 Temperature sensor
142 Level sensor
144 Outlet pipe
146 Drain pump
148 Outlet
150 Dosing system
152 Rinse pipe system
154 Cleaning fluid, rinse fluid
156 Rinse tank
158 Rinse tank heating means
160 Temperature sensor
162 Level sensor
164 Inlet
166 Valve
168 Dosing system
170 Reverse osmosis device
172 Pressure booster pump
174 Holder
175 Product range
176 Control means
178 Basic basket
180 Bottom part
182 Side walls
184 Edge
186 Frame
188 Edge protection
190 Positioning aids
192 Carrying handles 194 First holder
196 Breathing masks
198 Breathing valve
200 First set
202 Small parts basket
204 Inner mask
206 Mask holding device
208 Framework
210 Holding bracket for breathing mask
212 Holding bracket for inner mask
213 Hold-down device for inner mask
214 Receiving means
216 Breathing valve holding device
218 Friction brakes
220 Pressurizing device
222 Pressure connection
224 Compressed air supply
226 Hose
228 Pressurized gas line
230 Frame
232 Coupling
234 Cap
236 Coupling
238 Apparatus-side pressurizing device
240 Pressurized gas source
242 Valve
244 Supporting corners
246 Connecting element
248 Cover
250 Opening
252 Vision window
254 Inside surface
256 Holding strap
258 Air hose
260 Second holder
262 Second set
264 Frame
266 Carrying framework
267 Carrying framework holding device
268 Support
270 Flat plate
272 Cross struts
274 Carrying belt
276 Third holder
278 Third set
280 Fourth holder
282 Fourth set

The invention claimed is:

1. A product range for cleaning breathing apparatuses, including at least two holders, wherein the holders include:
   a first holder for cleaning breathing masks and breathing valves, including at least one mask holding device for positioning at least one breathing mask, additionally comprising at least one breathing valve holding device for positioning at least one breathing valve and at least one pressurizing device with at least one pressure connection, wherein the pressure connection is connectable to the breathing valve and wherein the pressurizing device is set up to apply compressed air to the breathing valve during cleaning; and
   at least one second holder for cleaning carrying frameworks for pressurized gas cylinders for breathing apparatuses, including at least one carrying framework holding device for positioning at least one carrying framework,
   wherein the holders are dimensioned in such a manner that they can be moved into a cleaning apparatus for cleaning the breathing apparatuses so as to be exchangeable,
   wherein the holders comprise in each case a basic basket including a bottom part, side walls and positioning aids provided on an upper circumferential edge of the side walls,
   wherein the holders further comprise in each case at least one set including supporting corners configured to be received in the positioning aids of the basic basket to fit the at least one set into the basic basket.

2. The product range as claimed in claim 1, wherein the mask holding device includes a framework, wherein the framework comprises at least one holding bracket for the at least one breathing mask, wherein the breathing mask can be put over the holding bracket.

3. The product range as claimed in claim 2, wherein the framework additionally comprises at least one further holding bracket for at least one inner mask.

4. The product range as claimed in claim 1, wherein the breathing valve holding device comprises at least one receiving means into which a connecting piece of the breathing valve is pluggable and in which the connecting piece is held in a fixed manner once it has been plugged in.

5. The product range as claimed in claim 1, wherein the pressurizing device comprises at least one compressed air supply, wherein the compressed air supply opens out into a pressurized gas line, wherein the pressure connection is fitted onto the pressurized gas line, wherein the pressurized gas line is developed as a carrying component and carries at least the breathing valve holding device.

6. The product range as claimed in claim 1, wherein the first holder is set up to receive a plurality of breathing masks and a plurality of breathing valves and comprises a plurality of mask holding devices and a plurality of breathing valve holding devices as well as a plurality of pressure connections.

7. The product range as claimed in claim 6, wherein the mask holding devices and the breathing valve holding devices are arranged in an alternating manner along a periphery of the first holder.

8. The product range as claimed in claim 1, wherein the first holder additionally comprises at least one small parts basket, wherein the small parts basket is set up for receiving accessory parts during a cleaning operation.

9. The product range as claimed claim 8, wherein a plurality of small parts baskets is provided, wherein the first holder is set up for cleaning a plurality of breathing masks and a plurality of breathing valves, wherein each pair consisting of one breathing mask and one breathing valve has assigned thereto in each case one small parts basket.

10. The product range as claimed in claim 1, wherein the carrying framework holding device comprises at least one support which projects upward from the second holder.

11. The product range as claimed in claim 10, wherein the second holder additionally comprises a frame, wherein the support is connected to the frame by a plurality of cross struts and is stabilized thereby.

12. The product range as claimed in claim 1, wherein the product range additionally comprises at least one third holder for cleaning breathing valves, wherein the third holder comprises at least one breathing valve holding device for positioning at least one breathing valve, wherein the third holder additionally comprises at least one pressurizing device with at least one pressure connection, wherein the pressure connection is connectable to the breathing valve and wherein the pressurizing device is set up to apply pressurized gas to the breathing valves during cleaning.

13. The product range as claimed in claim 1, wherein the product range additionally comprises at least one fourth holder for cleaning breathing masks, comprising at least one mask holding device for positioning at least one breathing mask.

14. The product range as claimed in claim 1, wherein the basic basket of the holders is structurally the same and wherein the sets of the holders differ.

15. The product range as claimed in claim 14, wherein the sets are in each case connectable in a reversible manner to the associated basic basket.

16. A cleaning system for cleaning breathing apparatuses, including:
   at least one cleaning apparatus, including at least one cleaning chamber for receiving at least one breathing apparatus, wherein the cleaning apparatus additionally comprises at least one fluid device for applying at least one cleaning fluid to the breathing apparatus, and
   at least one product range as claimed in claim 1, wherein the holders of the product range are receivable in a selective manner in the cleaning chamber, wherein said cleaning apparatus is set up to use the first holder in at least one cleaning step and to apply pressurized gas in said cleaning step by means of the pressure connection to at least one breathing valve received in the first holder.

17. A method for cleaning breathing apparatuses, wherein the cleaning system is used as claimed in claim 16, wherein the method includes at least one first cleaning step and at least one second cleaning step,
   wherein in the first cleaning step the first holder is used, wherein at least one breathing mask is moved into the mask holding device of the first holder, wherein at least one breathing valve is moved into the breathing valve holding device, wherein pressurized gas is applied to the breathing valve by means of the pressure connection and the cleaning fluid is applied to the breathing mask and the breathing valve by means of the fluid device,
   wherein in the second cleaning step the second holder is used, wherein at least one carrying framework for pressurized gas cylinders for breathing apparatuses is moved into the carrying framework holding device, wherein the cleaning fluid is applied to the carrying framework by means of the fluid device.

* * * * *